US009518120B2

(12) United States Patent
Klinguer-Hamour et al.

(10) Patent No.: US 9,518,120 B2
(45) Date of Patent: Dec. 13, 2016

(54) ANTI-CXCR4 ANTIBODY AND ITS USE FOR THE DETECTION AND DIAGNOSIS OF CANCER

(75) Inventors: Christine Klinguer-Hamour, Groisy (FR); Alexandra Jouhanneaud, Bonneville (FR); Marie-Claire Janin-Bussat, Saint-Julien-en-Genevois (FR)

(73) Assignee: Pierrre Fabre Medicament, Boulogne-Billancourt (FR)

(*) Notice: Subject to any disclaimer, the term of this patent is extended or adjusted under 35 U.S.C. 154(b) by 3 days.

(21) Appl. No.: 14/235,274

(22) PCT Filed: Jul. 30, 2012

(86) PCT No.: PCT/EP2012/064883
§ 371 (c)(1),
(2), (4) Date: Jan. 27, 2014

(87) PCT Pub. No.: WO2013/017566
PCT Pub. Date: Feb. 7, 2013

(65) Prior Publication Data
US 2014/0170681 A1 Jun. 19, 2014

Related U.S. Application Data

(60) Provisional application No. 61/513,331, filed on Jul. 29, 2011.

(30) Foreign Application Priority Data

Jul. 29, 2011 (EP) ..................... 11306001

(51) Int. Cl.
*C07K 16/28* (2006.01)
*G01N 33/574* (2006.01)
(52) U.S. Cl.
CPC ....... *C07K 16/2896* (2013.01); *C07K 16/2866* (2013.01); *G01N 33/574* (2013.01); *C07K 2317/30* (2013.01); *C07K 2317/565* (2013.01)
(58) Field of Classification Search
CPC ............ C07K 16/2896; C07K 16/2866; C07K 2317/30; C07K 2317/565; G01N 33/574
See application file for complete search history.

(56) References Cited

FOREIGN PATENT DOCUMENTS

| EP | 1 674 111 A1 | 6/2006 |
|----|----|----|
| EP | 2 172 485 A1 | 4/2010 |
| WO | WO99/50461 A1 | 10/1999 |
| WO | WO01/85196 A2 | 11/2001 |
| WO | WO01/94420 A1 | 12/2001 |
| WO | WO03/090512 A1 | 11/2003 |
| WO | WO2004/059285 A1 | 7/2004 |
| WO | WO2008/060367 A2 | 5/2008 |
| WO | WO2009/140124 A1 | 11/2009 |
| WO | WO2010/037831 A1 | 4/2010 |

OTHER PUBLICATIONS

Angers, S., et al., "Detection of β$_2$-adrenergic Receptor Dimerization in Living Cells Using Bioluminescence Resonance Energy Transfer (BRET)," *PNAS*, 97:3684-3689, (2000).
Bachelder, R.E., et al., "Vascular Endothelial Growth Factor Promotes Breast Carcinoma Invasion in an Autocrine Manner By Regulating the Chemokine Receptor CXCR4," *Can. Res.*, 62:7203-7206, (2002).
Balkwill, F. "Cancer and the Chemokine Network," *Nat. Rev. Can.*, 4:540-550, (2004).
Barbero, S., et al., "Expression of the Chemokine Receptor CXCR$^4$ and Its Ligand Stromal Cell-Derived Factor 1 in Human Brian Tumors and Their Involvement in Glial Proliferation in Vitro," *Ann. N.Y. Acad. Sci.* 973:60-29, (2002).
Barbero, S., et al., "Stromal Cell-derived Factor 1 a Stimulates Human Glioblastoma Cell Growth through the Activation of Both Extracellular Signal-regulated Kinases ½ and Akt$^1$," *Can. Res.*, 63:1969-1974, (2003).
Bes, C., et al., "Efficient CD4 Binding and Immunosuppresive Properties of the 13B8.2 Monoclonal Antibody are Displayed by its CDR-H1-Derived Peptide CB11," *FEBS Letters*, 508:67-74, (2001).
DeFalco, V., et al., "Biological Role and Potential Therapeutic Targeting of the Chemokine Receptor CXCR4 in Undifferentiated Thyroid Cancer," *Can. Res.*, 67:11821-11829, (2007).
Fischer, T., et al., "Reassessment of CXCR4 Chemokine Receptor Expression in Human Normal and Neoplastic Tissues Using the Novel Rabbit Monoclonal Antibody UMB-2," *PLoS One*, 3:1-7, (2008).
Furusato, B., et al., "CXCR4 and Cancer," *Path. Int.*, 60:497-505, (2010).
Harvey, J., et al., "Estrogen Receptor Status by Immunohistochemistry Is Superior to the Ligand-Binding Assay for Predicting Response to Adjuvant Endocrine Therapy in Breast Cancer," *J. Clin Onc.*, 17:1474-1481, (1999).
Hereld, D., et al., "Slamming the DOR on Chemokine Receptor Signaling:Heterodimerization Silences Ligand-Occupied CXCR4 and δ-opiod Receptors," *Eur. J. Imm.*, 38:334-337, (2008).
Juarez, J., et al., "Chemokines and Their Receptors as Therapeutic Targets: The Role of the SDF-1/CXCR4 Axis," *Curr. Pharm. Des.*, 10:1245-1259, (2004).
Kaas, Q., et al., "IMGT/3Dstructure-DB and IMGT/StructuralQuery, a Database and a Tool for Immunoglobulin, T Cell Receptor and MHC Structural Data," *Nucl. Acids Res.*, 32:D208-D210, (2004).
Kass, Q., et al., "IMGT Colliers de Perles: Standardized Sequence-Structure Representations of the IgSF and MheSF Superfamily Domains," *Curr. Bio.*, 2:21-30, (2007).
Kato, M., et al., "Expression Pattern of CXC Chemokine Receptor-4 is Correlated with Lymph Node Metastasis in Human Invasive Ductal Carcinoma," *Breast Can. Res.*, 5:144-150, (2003).

(Continued)

*Primary Examiner* — Ruixiang Li
(74) *Attorney, Agent, or Firm* — Finnegan, Henderson, Farabow, Garrett & Dunner, L.L.P.

(57) ABSTRACT

The present invention provides a novel, isolated anti-CXCR4 antibody for use in the diagnosis of cancer. In particular, the antibody of the invention recognizes monomeric and homodimeric CXCR4, but not heterodimeric CXCR4.

17 Claims, 7 Drawing Sheets

(56) References Cited

OTHER PUBLICATIONS

Kohl, A., et al., "Designed to be Stable: Crystal Structure of a Consensus Ankyrin Repeat Protein," *PNAS*, 100:1700-1705, (2003).
Koshiba, T., et al., "Expression of Stromal Cell-derived Factor 1 and CXCR4 Ligand Receptor System in Pancreatic Cancer: A Possible Role for Tumor Progression," *Clin. Can. Res.*, 6:3530-3535, (2000).
Kucia, M., et al., "Trafficking of Normal Stem Cells and Metastasis of Cancer Stem Cells Involve Similar Mechanisms: Pivotal Role of the SDF-1-CXCR4 Axis," *Stem Cells*, 23:879-894, (2005).
Lee, H.J., et al., "Chemokine Receptor CXCR4 Expression, Function, and Clinical Implications in Gastric Cancer," *Int. J. Onc.*, 34:473-480, (2009).
LeFranc, M.P., et al., "Unique Database Numbering System for Immunogenetic Analysis," *Imm. Today*, 18:509, (1997).
LeFranc, M.P., et al., "The IMGT Unique Numbering for Immunoglobulins, T-Cell Receptors, and Ig-Like Domains," *The Imm.*, 7:132-136, (1999).
LeFranc, M.P., et al., "IMGT Unique Numbering for Immunoglobulin and T Cell Receptor Variable Domains and Ig Superfamily V-like Domains," *Devl. & Comp. Imm.*, 27:55-77, (2003).
Liang, Z., et al., "Silencing of CXCR4 Blocks Breast Cancer Metastasis," *Can. Res.*, 65:967-971, (2005).
Mantovani, A., et al, "The Chemokine System in Diverse Forms of Macrophage Activation and Polarization," *Trends in Imm.*, 25:677-686, (2004).
Muller, A., et al., "Involvement of Chemokine Receptors in Breast Cancer Metastasis," *Nature*, 410:50-56, (2001).
Murphy, P.M., "Chemokines and the Molecular Basis of Cancer Metastasis," *N. Engl. J. Med.*, 345:833-835, (2001).
Needleman, S.B., et al., "A General Method Applicable to the Search for Similarities in the Amino Acid Sequence of Two Proteins," *J. Mol. Biol.*, 48:443-453, (1970).
Ottaiano, A., et al., "Inhibitory Effects of Anti-CXCR4 Antibodies on Human Colon Cancer Cells," *Cancer Immunology, Immunotherapy*, 54:781-791(2004).
Owen, J.D., et al., "Enhanced Tumor-Forming Capacity for Immortalized Melanocytes Expressing Melanoma Growth Stimulatory Activity/Growth-Regulated Cytokine β and γ Proteins," *Int. J. Cancer*, 73:94-103, (1997).
Pagano, L., "The potential role of CXCR4 and SDF-1 as Indicators of Tumor Aggressiveness in Patients With Conventional Papillary Thyroid Carcinoma," *Tesi di Dottorato, Universita Degli Studi di Napoli Federico II*, (2008).
Payne, S.J.L., et al., "Predictive Markers in Breast Cancer—the Present," *Histopathology*, 52, 82-90 (2008).
Pearson, W.R. et al., "Improved Tools for Biological Sequence Comparison," *Proc. Natl. Acd. Sci.*, 85:2444-2448, (1988).
Percherancier, Y., "Bioluminescence Resonance Energy Transfer Reveals Ligand-induced Conformational Changes in CXCR4 Homo- and Heterodimers*," XP-002511383, *J. Bio. Chem.*, 280:9895-9903, (2005).
Phillips, R., et al., "The Stromal Derived Factor-1/CXCL12-CXC Chemokine Receptor 4 Biological Axis in Non-Small Cell Lung Cancer Metastases," *Am. J. Resp. and Critical Care Medicine*, 167:1676-1686, (2003).

Romagnani, P., et al., "CXC Chemokines: the Regulatory Link Between Inflammation and Angiogenesis," *Trends in Immunology*, 25:201-209, (2004).
Rubin, J.B., et al., "A Small-Molecule Antagonist of CXCR4 Inhibits Intracranial Growth of Primary Brain Tumors," *PNAS*, 100: 13513-13518, (2003).
Ruiz, M., et al., "IMGT Gene Identification and Colliers de Peries of Human Immunoglobulins with Known 3D Structures," 53:857-883 *Immunogenetics*, (2002).
Salanga, C.L., et al., "Modulation of Chemokine Receptor Activity Through Dimerization and Crosstalk," *Cell. Mol. Life Sci.* 66:1370-1386, (2009).
Schimanski, C.C., et al., "Expressio of Chemokine Receptor CXCR4 Correlates with Progression of Pancreatic Cancer," *J. Clin. Onc.*, 18S:14018, (2006).
Scotton[1], C.J., et al., "Multiple Actions of the Chemokine CXCL 12 on Epithelial Tumor Cells in Human Ovarian Cancer," *Can. Res.*, 62:5930-598, (2002).
Sierro, F., et al., "Disrupted Cardiac Development but Normal Hematopoiesis in Mice Deficient in the Second CXCL12/SDF-1 Receptor, CXCR7," *PNAS*, 104:14759-14764, (2007).
Simpson, J.F., et al., "Prognostic Value of Histologic Grade and Proliferative Activity in Axillary Node-Positive Breast Cancer: Results From the Eastern Cooperative Oncology Group Companion Study, EST 4189," *J. Clinical Oncology*,18: 2059-2069, (2000).
Singh, R.K., et al., "Expession of Interleukin 8 Correlates with the Metastatic Potential of Human Melanoma Cells in Nude Mice," *Cancer Research* 54:3242-3247, (1994).
Skerra, A., "Engineered Protein Scaffolds for Molecular Recognition," *J. Mol. Rec.*, 13:167-187, (2000).
Smith, F.T., et al., "Comparison of Biosequences," *Adv. App. Math.*, 2:482-489, (1981).
Stewart, J.M., et al., "Solid Phase Peptide Synthesis," *Pierce Chem. Co.*, 111, $2^{nd}$ Edition, (1984).
Strieter, R.M., "CXC Chemokines in Angiogenesis of Cancer," *Sem. Can. Bio.*, 14:195-200, (2004).
Sun, Y., et al., "Expression of CXCR4 and CXCL12 (SDF-1) in Human Prostate Cancers (PCa) In Vivo," *J. Cellular Biochemistry*, 89:462-473, (2003).
Tamamura, H., et al., "T140 Analogs as CXCR4 Antagonists Identified as Anti-Metastatic Agents in the Treatment of Breast Cancer," *FEBS Letters*, 550:79-82, (2003).
Tanaka, T., et al., "Chemokines in Tumor Progression and Metastasis," *Cancer Sci.*, 96:317-322, (2005).
Tatusova, T., A., et al., "Blast 2 Sequences, a New Tool for Comparing Protein and Nucleotide Sequences," *FEMS Microbiology Letters*, 174:247-250, (1999).
Wang, J., et al., "Dimerization of CXCR4 in Living Malignant Cells: Control of Cell Migration by a Synthetic Peptide that Reduces Homologous CXCR4 Interactions," *Mol. Cancer Ther.*, 5:2474-83 (2006).
Wang, J., et al., "Dimerization of Chemokine Receptors in Living Cells: Key to Receptor Function and Novel Targets for Therapy," *Drug Discovery Today*, 13:625-632, (Jul. 2008).
Wilson, S., et al., "The CXCR1 and CXCR2 Receptors Form Constitutive Homo- and Heterodimers Selectively and with Equal Apparent Affinities," *J. Bio. Chem.*, 280:28663-28674, (2005).
Zlotnik, A., et al., "Chemokines: A New Classification System and Their Role in Immunity," *Immunity*, 12:121-127, (2000).

SEQUENCE LISTING

<160> NUMBER OF SEQ ID NOS: 16

<210> SEQ ID NO 1
<211> LENGTH: 8
<212> TYPE: PRT
<213> ORGANISM: mus musculus

<400> SEQUENCE: 1

Gly Tyr Thr Phe Thr Glu Tyr Thr
1               5

<210> SEQ ID NO 2
<211> LENGTH: 8
<212> TYPE: PRT
<213> ORGANISM: mus musculus

<400> SEQUENCE: 2

Ile Asn Pro Ile Asn Gly Ala Thr

```
1               5
```

<210> SEQ ID NO 3
<211> LENGTH: 16
<212> TYPE: PRT
<213> ORGANISM: mus musculus

<400> SEQUENCE: 3

```
Cys Ala Arg Lys Gly Tyr Val Ser Asp Pro Tyr Thr Met Asp Tyr Trp
1               5                   10                  15
```

<210> SEQ ID NO 4
<211> LENGTH: 11
<212> TYPE: PRT
<213> ORGANISM: mus musculus

<400> SEQUENCE: 4

```
Gln Ser Leu Val His Ser Asn Gly Asn Thr Tyr
1               5                   10
```

<210> SEQ ID NO 5
<211> LENGTH: 3
<212> TYPE: PRT
<213> ORGANISM: mus musculus

<400> SEQUENCE: 5

```
Lys Val Ser
1
```

<210> SEQ ID NO 6
<211> LENGTH: 9
<212> TYPE: PRT
<213> ORGANISM: mus musculus

<400> SEQUENCE: 6

```
Ser Gln Ser Thr His Val Pro Trp Thr
1               5
```

<210> SEQ ID NO 7
<211> LENGTH: 121
<212> TYPE: PRT
<213> ORGANISM: mus musculus

<400> SEQUENCE: 7

```
Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Tyr
            20                  25                  30

Thr Ile His Trp Val Met Gln Ser His Val Glu Ser Leu Glu Trp Ile
        35                  40                  45

Gly Gly Ile Asn Pro Ile Asn Gly Ala Thr Thr Tyr Asn Gln Lys Phe
    50                  55                  60

Arg Gly Lys Ala Thr Leu Thr Val Gly Lys Ser Ser Thr Ala Tyr
65                  70                  75                  80

Met Ala Leu Arg Ser Leu Thr Ser Glu Asp Ser Ala Val Phe Tyr Cys
                85                  90                  95

Ala Arg Lys Gly Tyr Val Ser Asp Pro Tyr Thr Met Asp Tyr Trp Gly
            100                 105                 110

Gln Gly Thr Ser Val Thr Val Ser Ser
        115                 120
```

```
<210> SEQ ID NO 8
<211> LENGTH: 112
<212> TYPE: PRT
<213> ORGANISM: mus musculus

<400> SEQUENCE: 8

Asp Val Val Met Thr Gln Ser Pro Leu Ser Leu Pro Val Ser Leu Gly
1               5                   10                  15

Asp Gln Ala Ser Phe Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110

<210> SEQ ID NO 9
<211> LENGTH: 24
<212> TYPE: DNA
<213> ORGANISM: mus musculus

<400> SEQUENCE: 9
ggatacacat tcactgaata cacc                                          24

<210> SEQ ID NO 10
<211> LENGTH: 24
<212> TYPE: DNA
<213> ORGANISM: mus musculus

<400> SEQUENCE: 10
attaatccga tcaatggtgc tact                                          24

<210> SEQ ID NO 11
<211> LENGTH: 48
<212> TYPE: DNA
<213> ORGANISM: mus musculus

<400> SEQUENCE: 11
tgtgcaagaa agggctatgt ttccgaccct tatactatgg actactgg                48

<210> SEQ ID NO 12
<211> LENGTH: 33
<212> TYPE: DNA
<213> ORGANISM: mus musculus

<400> SEQUENCE: 12
cagagccttg tacacagtaa tggaaacacc tat                                33

<210> SEQ ID NO 13
<211> LENGTH: 9
<212> TYPE: DNA
<213> ORGANISM: mus musculus

<400> SEQUENCE: 13 aaagtttcc                                                            9
```

```
<210> SEQ ID NO 14
<211> LENGTH: 27
<212> TYPE: DNA
<213> ORGANISM: mus musculus

<400> SEQUENCE: 14
tctcaaagta cacatgttcc gtggacg                                      27

<210> SEQ ID NO 15
<211> LENGTH: 363
<212> TYPE: DNA
<213> ORGANISM: mus musculus

<400> SEQUENCE: 15
gaggtccagc tgcaacagtc tggacctgag ctggtgaagc ctggggcttc agtgaagatt   60
tcctgcaaga cttctggata cattcact gaatacacca tacactgggt gatgcagagc    120
catgtagaga gccttgagtg gattggaggt attaatccga tcaatggtgc tactacctac  180
aaccagaaat tcaggggcaa ggccacattg actgtaggca agtcctccag cacagcctac  240
atggccctcc gcagcctgac atctgaggat tctgcagtct tttactgtgc aagaaagggc  300
tatgtttccg acccttatac tatggactac tggggtcaag gaacctcagt caccgtctcc  360
tca                                                                363

<210> SEQ ID NO 16
<211> LENGTH: 336
<212> TYPE: DNA
<213> ORGANISM: mus musculus

<400> SEQUENCE: 16
gatgttgtga tgacccagtc tccactctcc ctgcctgtta gtcttggaga tcaagcctcc   60
ttctcttgca gatctagtca gagccttgta cacagtaatg gaaacaccta tttacattgg  120
tacctgcaga agccaggcca gtctccaaag ctcctaatct acaaagtttc caaccgcttt  180
tctggggtcc cagacaggtt cagtggcagt ggatctggga cagatttcac actcaagatc  240
agcagagtgg aggctgagga tctgggagtt tatttctgct ctcaaagtac acatgttccg  300
tggacgttcg gtggaggcac caagctggaa atcaaa                            336
```

ANTI-CXCR4 ANTIBODY AND ITS USE FOR THE DETECTION AND DIAGNOSIS OF CANCER

CROSS REFERENCE TO RELATED APPLICATIONS

This application is a national phase application based on PCT/EP2012/064883, filed Jul. 30, 2012, which claims the priority of European Application No. 11306001.6, filed Jul. 29, 2011, and the benefit of U.S. Provisional Application No. 61/513,331, filed Jul. 29, 2011, the contents of all of which are incorporated herein by reference.

The present invention relates to the field of prognosis and/or diagnosis and/or therapy monitoring of a proliferative disease in a patient. More particularly, the invention relates to an antibody capable of binding specifically to the CXCR4, as well as the amino acid and nucleic acid sequences coding for this antibody. The invention likewise comprises the use of said antibody, and corresponding processes, for detecting and diagnosing pathological hyperproliferative oncogenic disorders associated with expression of CXCR4. In certain embodiments, the disorders are oncogenic disorders associated with increased expression of CXCR4 relative to normal or any other pathology connected with the overexpression of CXCR4. The invention finally comprises products and/or compositions or kits comprising at least such antibody for the prognosis or diagnostic or therapy monitoring of certain cancers.

Chemokines are small, secreted peptides that control the migration of leukocytes along a chemical gradient of ligand, known as chemokine gradient, especially during immune reactions (Zlotnick A. et al., 2000). They are divided into two major subfamilies, CC and CXC, based on the position of their $NH_2$-terminal cysteine residues, and bind to G protein coupled receptors, whose two major sub families are designated CCR and CXCR. More than 50 human chemokines and 18 chemokine receptors have been discovered so far.

Many cancers have a complex chemokine network that influences the immune-cell infiltration of tumor, as well as tumor cell growth, survival, migration and angiogenesis. Immune cells, endothelial cells and tumor cells themselves express chemokine receptors and can respond to chemokine gradients. Studies of human cancer biopsy samples and mouse cancer models show that cancer cell chemokine-receptor expression is associated with increase metastatic capacity. Malignant cells from different cancer types have different profiles of chemokine-receptor expression, but Chemokine receptor 4 (CXCR4) is most commonly found. Cells from at least 23 different types of human cancers of epithelial, mesenchymal and haematopoietic origin express CXCR4 receptor (Balkwill F. et al., 2004).

Chemokine receptor 4 (also known as fusin, CD184, LESTR or HUMSTR) exists as two isoforms comprising 352 or 360 amino acids. Isoform a has the amino acid sequence depicted under the Genbank accession number NP_001008540, while isoform b has the amino acid sequence depicted under the Genbank accession number NP_003458. Residue Asn11 is glycosylated, residue Tyr21 is modified by the addition of a sulfate group and Cys 109 and 186 are bond with a disulfide bridge on the extracellular part of the receptor (Juarez J. et al., 2004).

This receptor is expressed by different kind of normal tissues, naïve, non-memory T-cells, regulatory T cells, B-cells, neutrophils, endothelial cells, primary monocytes, dendritic cells, Natural Killer cells, CD34+ hematopoietic stem cells and at a low level in heart, colon, liver, kidneys and brain. CXCR4 plays a key role in leukocytes trafficking, B cell lymphopoiesis and myelopoiesis.

CXCR4 receptor is over-expressed in a large number of cancers including but not limited to lymphoma, leukemia, multiple myeloma, colon (Ottaiano A. et al., 2004), breast (Kato M. et al., 2003), prostate (Sun Y. X. et al., 2003), lungs [small-cell- and non-small-cell-carcinoma (Phillips R. J. et al., 2003)], ovary (Scotton C. J. et al., 2002), pancreas (Koshiba T. et al., 2000), kidneys, brain (Barbero S et al., 2002), glioblastoma and lymphomas.

The unique ligand of CXCR4 receptor described so far is the Stromal-cell-Derived Factor-1 (SDF-1) or CXCL12. SDF-1 is secreted in large amount in lymph nodes, bone marrow, liver, lungs and to a less extent by kidneys, brain and skin CXCR4 is also recognized by an antagonistic chemokine, the viral macrophage inflammatory protein II (vMIP-II) encoded by human herpesvirus type III.

CXCR4/SDF-1 axis plays a key role in cancer and is implicated directly in migration, invasion leading to metastases. Indeed, cancer cells express CXCR4 receptor, they migrate and enter the systemic circulation. Then cancer cells are arrested in vascular beds in organs that produce high levels of SDF-1 where they proliferate, induce angiogenesis and form metastatic tumors (Murphy P M., 2001). This axis is also involved in cell proliferation via activation of Extracellular-signal-Regulated Kinase (ERK) pathway (Barbero S. et al., 2003) and angiogenesis (Romagnani P., 2004). Indeed, CXCR4 receptor and its ligand SDF-1 clearly promote angiogenesis by stimulating VEGF-A expression which in turns increases expression of CXCR4/SDF-1 (Bachelder R. E. et al., 2002). It is also known that tumor associated macrophages (TAM) accumulated in hypoxic areas of tumors and are stimulated to co-operate with tumor cells and promote angiogenesis. It was observed that hypoxia up-regulated selectively expression of CXCR4 in various cell types including TAM (Mantovani A. et al., 2004). It has been recently demonstrated that CXCR4/SDF-1 axis regulates the trafficking/homing of CXCR4+ hematopoietic stem/progenitor cells (HSC) and could play a role in neovascularization. Evidence indicates that besides HSC, functional CXCR4 is also expressed on stem cells from other tissues (tissue-committed stem cells=TCSCs) so SDF-1 may play a pivotal role in chemottracting CXCR4+ TCSCs necessary for organ/tissue regeneration but these TCSC may also be a cellular origin of cancer development (cancer stem cells theory). A stem cell origin of cancer was demonstrated for human leukemia and recently for several solid tumors such as brain and breast. There are several examples of CXCR4+ tumors that may derive from the normal CXCR4+ tissue/organ-specific stem cells such as leukemias, brain tumors, small cell lung cancer, breast cancer, hepatoblastoma, ovarian and cervical cancers (Kucia M. et al., 2005).

Targeting cancer metastases by interfering with CXCR4 receptor was demonstrated in vivo using a monoclonal antibody directed against CXCR4 receptor (Muller A. et al., 2001). Briefly, it was shown that a monoclonal antibody directed against CXCR4 receptor (Mab 173 R&D Systems) decreased significantly the number of lymph node metastases in an orthotopic breast cancer model (MDA-MB231) in SCID mice. Another study (Phillips R. J et al., 2003) also showed the critical role of SDF-1/CXCR4 axis in metastases in an orthotopic lung carcinoma model (A549) using polyclonal antibodies against SDF-1 but in this study there was no effect neither on tumor growth nor on angiogenesis. Several other studies described also the inhibition of either metastasis in vivo using siRNAs duplexes of CXCR4 (Liang Z. et al., 2005) biostable CXCR4 peptide antagonists (Tamamura H. et al., 2003) or tumor growth in vivo using small molecule antagonist of CXCR4 like AMD 3100 (Rubin J. B. et al., 2003; De Falco V. et al., 2007) or Mab (patent WO2004/059285 A2). Thus, CXCR4 is a validated therapeutic target for cancers.

Chemokine receptor 2 (CXCR2), another chemokine receptor is also described as an interesting target in oncology. Indeed, CXCR2 transmits an autocrine cell growth signal in several tumor cell types and can also affect tumor growth indirectly by promoting angiogenesis (Tanaka T. et al. 2005).

CXCR2 chemokine receptor encompasses 360 amino acids. It is expressed mainly in endothelial cells and especially during neovascularization. Several chemokines bind CXCR2 receptor: CXCL5, -6, -7, IL-8, GRO-$\alpha$, -$\beta$ and $\gamma$. which belong to ERL+ pro-angiogenic chemokines. The CXCR2 receptor share sequence homologies with CXCR4 receptor: 37% sequence identity and 48% sequence homology. The CXCR2/ligands axis is involved in several tumor growth mechanisms such as metastasis (Singh R K. et al., 1994) cell proliferation (Owen J. D. et al., 1997) and in ERL+ chemokines-mediated angiogenesis (Strieter R. M. et al., 2004; Romagnani et al., 2004). Finally, tumor-associated macrophages and neutrophils are key elements of inflammatory-induced tumor growth and chemokines such as CXCL5, IL-8 and GRO-$\alpha$ initiate neutrophils recruitment.

Dimerization has emerged as a universal mechanism for regulating the function of G-protein-coupled receptors, among these are chemokine receptors (Wang J. and Norcross M., 2008). Homo- and heterodimerization in response to chemokine binding has been shown to be required for the initiation and the alteration of signaling by a number of chemokine receptors. Growing evidence supports the concept that receptor dimers or oligomers are probably the basic functional unit of chemokine receptors. Chemokine receptor dimers are found in the absence of ligands and chemokines induce conformational changes of receptor dimers. CXCR4 is known to form homodimers but also heterodimers, for examples with the $\delta$-opioid receptor (DOR) (Hereld D., 2008) or CCR2 (Percherancier Y. et al., 2005). In the latter example, peptides derived from the transmembrane domains of CXCR4 inhibited activation by blocking the ligand-induced conformational transitions of the dimer (Percherancier Y. et al., 2005). Another study showed that CXCR4-TM4 peptide, a synthetic peptide of the transmembrane region of CXCR4, decreases energy transfer between protomers of CXCR4 homodimers and inhibits SDF-1-induced migration and actin polymerization in malignant cells (Wang J. et al., 2006). More recently, it was also described that CXCR7 formed functional heterodimers with CXCR4 and enhanced SDF-1-induced signaling (Sierro F. et al., 2007). Other examples of constitutive heterodimers include studies showing CXCR1 and CXCR2 interact as well as forming respective homodimers. No interactions were noted for either of them with another GPCR (alpha(1A)-adrenoreceptor), indicating the specificity of CXCR1 and CXCR2 interaction (Wilson S. et al., 2005).

As previously mentioned, CXCR4 and CXCR2 receptors are interesting tumor targets. Interfering with those receptors should inhibit tumor growth and metastases in a very efficient way, by decreasing tumor cell proliferation, angiogenesis, tumor cell migration and invasion, neutrophils and macrophages recruitment by tumors and by inhibiting CXCR4 cancer stem cells.

The applicant has already disclosed monoclonal antibodies, referred as 515H7 and 414H5, which bind and induce conformational changes of both CXCR4/CXCR4 homodimers and CXCR4/CXCR2 heterodimers, and have strong anti-tumoral activities (see WO 2010/037831).

The present invention aims at providing at least one reagent that can be used as a diagnosis or prognosis tool for detecting and/or monitoring oncogenic disorders, especially those characterized by CXCR4 expression or mediated by aberrant CXCR4 expression.

Specifically, the invention provides a novel isolated antibody capable of binding CXCR4 which can be used for diagnosis or prognosis purposes.

Surprisingly, and in contrast to the antibodies of the prior art, the applicant has generated an present antibody is capable of binding specifically to CXCR4, expressed as a CXCR4 monomer or as a CXCR4/CXCR4 homodimer. T On the other hand, the antibody of the invention does not significantly bind to any of the known CXCR4/X heterodimers and, more particularly, not to, including the CXCR4/CXCR2 heterodimer. As it will be discussed in the present specification herebelow, this property is of great interest regarding the field of diagnosis.

Other features and advantages of the invention will be apparent from the detailed description and examples that followed.

In a first aspect, the invention relates to an isolated antibody, or one of its antigen-binding fragment or derivative, that binds to CXCR4 with high affinity, preferably to human CXCR4, and can thus be useful for diagnosing pathological hyperproliferative oncogenic disorders mediated by CXCR4 expression.

Other features and advantages of the invention will be apparent from the detailed description and examples that followed.

Preferably, the invention encompasses the antibodies, their derived compounds or their functional fragments, according to the present invention, obtained by genetic recombination or chemical synthesis.

In a first embodiment, the antibody of the invention is a monoclonal antibody.

A "monoclonal antibody" is understood to mean an antibody arising from a nearly homogeneous antibody population. More particularly, the individual antibodies of a population are identical except for a few possible naturally-occurring mutations which can be found in minimal proportions. In other words, a monoclonal antibody consists of a homogeneous antibody arising from the growth of a single cell clone (for example a hybridoma, a eukaryotic host cell transfected with a DNA molecule coding for the homogeneous antibody, a prokaryotic host cell transfected with a DNA molecule coding for the homogeneous antibody, etc.) and is generally characterized by heavy chains of one and only one class and subclass, and light chains of only one type. Monoclonal antibodies are highly specific and are directed against a single antigen. In addition, in contrast with preparations of polyclonal antibodies which typically include various antibodies directed against various determinants, or epitopes, each monoclonal antibody is directed against a single epitope of the antigen.

A typical IgG antibody is composed of two identical heavy chains and two identical light chains that are joined by disulfide bonds. Each heavy and light chain contains a constant region and a variable region. Each variable region contains three segments called "complementarity-determining regions" ("CDRs") or "hypervariable regions", which are primarily responsible for binding an epitope of an antigen. They are usually referred to as CDR1, CDR2, and CDR3, numbered sequentially from the N-terminus. The more highly conserved portions of the variable regions are called the "framework regions".

Three heavy chain CDRs and 3 light chain CDRs exist. The term CDR or CDRs is used here in order to indicate, according to the case, one of these regions or several, or even the whole, of these regions which contain the majority of the amino acid residues responsible for the binding by affinity of the antibody for the antigen or the epitope which it recognizes.

According to the invention, the CDRs of the antibody will be defined according to the IMGT numbering system. It will be obvious for the man skilled in the art to deduce the CDRs according to Kabat from the CDRs according to IMGT. The CDRs according to Kabat must be considered as part of the scope of the invention.

The IMGT unique numbering has been defined to compare the variable domains whatever the antigen receptor, the chain type, or the species [Lefranc M.-P., Immunology Today 18, 509 (1997)/Lefranc M.-P., The Immunologist, 7, 132-136 (1999)/Lefranc, M.-P., Pommié, C., Ruiz, M., Giudicelli, V., Foulquier, E., Truong, L., Thouvenin-Contet, V. and Lefranc, Dev. Comp. Immunol., 27, 55-77 (2003)]. In the IMGT unique numbering, the conserved amino acids always have the same position, for instance cysteine 23 (1st-CYS), tryptophan 41 (CONSERVED-TRP), hydrophobic amino acid 89, cysteine 104 (2nd-CYS), phenylalanine or tryptophan 118 (J-PHE or J-TRP). The IMGT unique numbering provides a standardized delimitation of the framework regions (FR1-IMGT: positions 1 to 26, FR2-IMGT: 39 to 55, FR3-IMGT: 66 to 104 and FR4-IMGT: 118 to 128) and of the complementarity determining regions: CDR1-IMGT: 27 to 38, CDR2-IMGT: 56 to 65 and CDR3-IMGT: 105 to 117. As gaps represent unoccupied positions, the CDR-IMGT lengths (shown between brackets and separated by dots, e.g. [8.8.13]) become crucial information. The IMGT unique numbering is used in 2D graphical representations, designated as IMGT Colliers de Perles [Ruiz, M. and Lefranc, M.-P., Immunogenetics, 53, 857-883 (2002)/Kaas, Q. and Lefranc, M.-P., Current Bioinformatics, 2, 21-30 (2007)], and in 3D structures in IMGT/3Dstructure-DB [Kaas, Q., Ruiz, M. and Lefranc, M.-P., T cell receptor and MHC structural data. Nucl. Acids. Res., 32, D208-D210 (2004)].

In a preferred embodiment, the antibody of the invention, or the antigen-binding fragment or derivative thereof, comprises at least one complementary determining region (CDR) having an amino acid sequence selected from the group of amino acid sequences SEQ ID NOs. 1 to 6, or at least one CDR whose sequence has at least 80%, preferably 85%, 90%, 95% and 98% identity after optimal alignment with sequences SEQ ID NOs 1 to 6.

In a more preferred embodiment, the antibody of the invention comprises i) a heavy chain comprising at least one of the following CDR-H1, CDR-H2 and CDR-H3, as defined according to IMGT numbering system, wherein CDR-H1 comprises the sequence SEQ ID No. 1, CDR-H2 comprises the sequence SEQ ID No. 2 and CDR-H3 comprises the sequence SEQ ID No. 3; and/or ii) a light chain comprising at least one of the following CDR-L1, CDR-L2 and CDR-L3, as defined according to IMGT numbering system, wherein CDR-L1 comprises the sequence SEQ ID No. 4, CDR-L2 comprises the sequence SEQ ID No. 5 and CDR-L3 comprises the sequence SEQ ID No. 6.

In a further preferred embodiment, the antibody of the invention, or an antigen-binding fragment or derivative thereof, comprises a heavy chain, said heavy chain comprising the following three CDRs as defined according to IMGT, respectively CDR-H1, CDR-H2 and CDR-H3, wherein CDR-H1 comprises the sequence SEQ ID No. 1, CDR-H2 comprises the sequence SEQ ID No. 2 and CDR-H3 comprises the sequence SEQ ID No. 3.

According to another preferred embodiment, the antibody of the invention, or an antigen-binding fragment or derivative thereof, comprises a light chain, said light chain comprising the following three CDRs as defined according to IMGT, respectively CDR-L1, CDR-L2 and CDR-L3, wherein CDR-L1 comprises the sequence SEQ ID No. 4, CDR-L2 comprises the sequence SEQ ID No. 5 and CDR-L3 comprises the sequence SEQ ID No. 6.

In a preferred embodiment, the antibody of the invention, or a functional fragment or derivative thereof, comprises a heavy chain, said heavy chain comprising the following three CDRs, respectively CDR-H1, CDR-H2 and CDR-H3, wherein:
  CDR-H1 comprises the sequence SEQ ID No. 1, or a sequence with at least 80%, preferably 85%, 90%, 95% and 98% identity after optimal alignment with sequence SEQ ID No. 1;
  CDR-H2 comprises the sequence SEQ ID No. 2, or a sequence with at least 80%, preferably 85%, 90%, 95% and 98% identity after optimal alignment with sequence SEQ ID No. 2; and
  CDR-H3 comprises the sequence SEQ ID No. 3, or a sequence with at least 80%, preferably 85%, 90%, 95% and 98% identity after optimal alignment with sequence SEQ ID No. 3.

In another preferred embodiment, the antibody of the invention, or a functional fragment or derivative thereof, comprises a light chain, said light chain comprising the following three CDRs, respectively CDR-L1, CDR-L2 and CDR-L3, wherein:
  CDR-L1 comprises the sequence SEQ ID No. 4, or a sequence with at least 80%, preferably 85%, 90%, 95% and 98% identity after optimal alignment with sequence SEQ ID No. 4;
  CDR-L2 comprises the sequence SEQ ID No. 5, or a sequence with at least 80%, preferably 85%, 90%, 95% and 98% identity after optimal alignment with sequence SEQ ID No. 5; and
  CDR-L3 comprises the sequence SEQ ID No. 6, or a sequence with at least 80%, preferably 85%, 90%, 95% and 98% identity after optimal alignment with sequence SEQ ID No. 6.

In still another embodiment, the antibody, or functional fragment or derivative thereof, comprises:
  a heavy chain, said heavy chain comprising the following three CDRs as defined according to IMGT, respectively CDR-H1 having the sequence SEQ ID No. 1, CDR-H2 having the sequence SEQ ID No. 2 and CDR-H3 having the sequence SEQ ID No. 3, or a sequence having at least 80%, preferably 85%, 90%, 95% and 98% identity after optimal alignment with sequences SEQ ID Nos. 1, 2 or 3, respectively; and
  a light chain comprising the following three CDRs as defined according to IMGT, respectively CDR-L1 having the sequence SEQ ID No. 4, CDR-L2 having the sequence SEQ ID No. 5 and CDR-L3 having the sequence SEQ ID No. 6, or a sequence having at least 80%, preferably 85%, 90%, 95% and 98% identity after optimal alignment with sequences SEQ ID Nos. 4, 5 or 6, respectively.

In the sense of the present invention, the "percentage identity" between two sequences of nucleic acids or amino acids means the percentage of identical nucleotides or amino acid residues between the two sequences to be compared, obtained after optimal alignment, this percentage being purely statistical and the differences between the two sequences being distributed randomly along their length. The comparison of two nucleic acid or amino acid sequences is traditionally carried out by comparing the sequences after having optimally aligned them, said comparison being able to be conducted by segment or by using an "alignment window". Optimal alignment of the sequences for comparison can be carried out, in addition to comparison by hand, by means of the local homology algorithm of Smith and Waterman (1981) [Ad. App. Math. 2:482], by means of the local homology algorithm of Neddleman and Wunsch (1970) [J. Mol. Biol. 48:443], by means of the similarity search method of Pearson and Lipman (1988) [Proc. Natl. Acad. Sci. USA 85:2444] or by means of computer software using these algorithms (GAP, BESTFIT, FASTA and TFASTA in the Wisconsin Genetics Software Package, Genetics Computer Group, 575 Science Dr., Madison, Wis., or by the comparison software BLAST NR or BLAST P).

The percentage identity between two nucleic acid or amino acid sequences is determined by comparing the two optimally-aligned sequences in which the nucleic acid or amino acid sequence to compare can have additions or deletions compared to the reference sequence for optimal alignment between the two sequences. Percentage identity is calculated by determining the number of positions at which the amino acid or nucleotide residue is identical between the two sequences, dividing the number of identical positions by the total number of positions in the alignment window and multiplying the result by 100 to obtain the percentage identity between the two sequences.

For example, the BLAST program, "BLAST 2 sequences" (Tatusova et al., "Blast 2 sequences—a new tool for comparing protein and nucleotide sequences", FEMS Microbiol., 1999, Lett. 174:247-250) available on the site http://www.ncbi.nlm.nih.gov/gorf/b12.html, can be used with the default parameters (notably for the parameters "open gap penalty": 5, and "extension gap penalty": 2; the selected matrix being for example the "BLOSUM 62" matrix proposed by the program); the percentage identity between the two sequences to compare is calculated directly by the program.

For the amino acid sequence exhibiting at least 80%, preferably 85%, 90%, 95% and 98% identity with a reference amino acid sequence, preferred examples include those containing the reference sequence, certain modifications, notably a deletion, addition or substitution of at least one amino acid, truncation or extension. In the case of substitution of one or more consecutive or non-consecutive amino acids, substitutions are preferred in which the substituted amino acids are replaced by "equivalent" amino acids. Here, the expression "equivalent amino acids" is meant to indicate any amino acids likely to be substituted for one of the structural amino acids without however modifying the biological activities of the corresponding antibodies and of those specific examples defined below.

Equivalent amino acids can be determined either on their structural homology with the amino acids for which they are substituted or on the results of comparative tests of biological activity between the various antibodies likely to be generated.

As a non-limiting example, table 1 below summarizes the possible substitutions likely to be carried out without resulting in a significant modification of the biological activity of the corresponding modified antibody; inverse substitutions are naturally possible under the same conditions.

TABLE 1

| Original residue | Substitution(s) |
|---|---|
| Ala (A) | Val, Gly, Pro |
| Arg (R) | Lys, His |
| Asn (N) | Gln |
| Asp (D) | Glu |
| Cys (C) | Ser |
| Gln (Q) | Asn |
| Glu (E) | Asp |
| Gly (G) | Ala |
| His (H) | Arg |
| Ile (I) | Leu |
| Leu (L) | Ile, Val, Met |
| Lys (K) | Arg |
| Met (M) | Leu |
| Phe (F) | Tyr |
| Pro (P) | Ala |
| Ser (S) | Thr, Cys |
| Thr (T) | Ser |
| Trp (W) | Tyr |
| Tyr (Y) | Phe, Trp |
| Val (V) | Leu, Ala |

As known by those skilled in the art, the greatest variability (length and composition) between the six CDRs is found at the three heavy-chain CDRs and, more particularly, at CDR-H3 of this heavy chain.

In a specific embodiment, the present invention relates to a murine antibody, or derived compounds or functional fragments of same.

In another embodiment, the invention discloses an antibody, as well as antigen-binding fragments and derivatives thereof, the said antibody comprising:

a heavy chain, said heavy chain comprising the following three CDRs, based on the "IMGT" definition of the CDRs:
CDR-H1 of the sequence SEQ ID No. 1 or of a sequence with at least 80%, preferably 85%, 90%, 95% and 98% identity after optimal alignment with sequence SEQ ID No. 1;
CDR-H2 of the sequence SEQ ID No. 2 or of a sequence with at least 80%, preferably 85%, 90%, 95% and 98% identity after optimal alignment with sequence SEQ ID No. 2; and
CDR-H3 of the sequence SEQ ID No. 3 or of a sequence with at least 80%, preferably 85%, 90%, 95% and 98% identity after optimal alignment with sequence SEQ ID No. 3, and a light chain, said light chain comprising the following three CDRs:
CDR-L1 of the sequence SEQ ID No. 4 or of a sequence with at least 80%, preferably 85%, 90%, 95% and 98% identity after optimal alignment with sequence SEQ ID No. 4;
CDR-L2 of the sequence SEQ ID No. 5 or of a sequence with at least 80%, preferably 85%, 90%, 95% and 98% identity after optimal alignment with sequence SEQ ID No. 5; and
CDR-L3 of the sequence SEQ ID No. 6 or of a sequence with at least 80%, preferably 85%, 90%, 95% and 98% identity after optimal alignment with sequence SEQ ID No. 6.

In a preferred embodiment, the invention relates to an antibody, or an antigen-binding fragment or derivative thereof, comprising i) a heavy chain comprising the following three CDRs, respectively CDR-H1 having the sequence SEQ ID No. 1, CDR-H2 having the sequence SEQ ID No. 2 and CDR-H3 having the sequence SEQ ID No. 3; and ii) a light chain comprising the following three CDRs, respectively CDR-L1 having the sequence SEQ ID No. 4, CDR-L2 having the sequence SEQ ID No. 5 and CDR-L3 having the sequence SEQ ID No. 6.

In another preferred embodiment of the invention, the said antibody, or antigen-binding fragment or derivative thereof, is selected among:

a) an antibody with a heavy chain comprising the following three CDRs, respectively CDR-H1 having the sequence SEQ ID No. 1, CDR-H2 having the sequence SEQ ID No. 2 and CDR-H3 having the sequence SEQ ID No. 3; and a light-chain variable domain comprising the sequence SEQ ID No. 8;

b) an antibody with a heavy chain variable domain comprising the sequence SEQ ID No. 7; and a light chain comprising the following three CDRs, respectively CDR-L1 having the sequence SEQ ID No. 4, CDR-L2 having the sequence SEQ ID No. 5 and CDR-L3 having the sequence SEQ ID No. 6; and c) an antibody with a heavy chain variable domain comprising the sequence SEQ ID No. 7; and a light-chain variable domain comprising the sequence SEQ ID No. 8.

According to still another embodiment, the invention relates to the antibody 427aB1, or one of its antigen-binding fragment or derivative, said antibody comprising a heavy-chain variable domain sequence comprising the amino acid sequence SEQ ID No. 7 or a sequence with at least 80%, preferably 85%, 90%, 95% and 98% identity after optimal alignment with sequence SEQ ID No. 7; and/or in that it comprises a light-chain variable domain sequence comprising the amino acid sequence SEQ ID No. 8, or a sequence with at least 80%, preferably 85%, 90%, 95% and 98% identity after optimal alignment with sequence SEQ ID No. 8.

In a further preferred embodiment, the invention provides an antibody 427aB1, or antigen-binding fragment or derivative thereof, said antibody 427aB1 comprising:

a) a heavy chain, said heavy chain comprising:
the following three CDRs, respectively CDR-H1 having the sequence SEQ ID No. 1, CDR-H2 having the sequence SEQ ID No. 2 and CDR-H3 having the sequence SEQ ID No. 3; and a light-chain variable domain comprising the sequence SEQ ID No. 8, and
a heavy chain variable domain, said heavy chain variable domain having the sequence SEQ ID No. 7; and b) a light chain, said light chain comprising:
the following three CDRs, respectively CDR-L1 having the sequence SEQ ID No. 4, CDR-L2 having the sequence SEQ ID No. 5 and CDR-L3 having the sequence SEQ ID No. 6; and
a light-chain variable domain, said light-chain variable domain having the sequence SEQ ID No. 8.

The invention also relates to any compound derived from an antibody as described in the invention.

An "antigen-binding derivative" or "derivative" of an antibody means in particular a binding protein composed of a peptide scaffold and at least one of the CDRs of the original antibody in order to preserve its ability to be recognized. Such derived compounds are well-known to a person skilled in the art.

In particular, the antibody of the invention, or a derived compound or antigen-binding fragment thereof, is characterized in that said derived compound consists of a binding protein comprising a peptide scaffold on which is grafted at least one CDR, the said CDR being grafted in such a way as to preserve all or part of the paratope recognition properties of the initial antibody. In a preferred embodiment, the said antigen-binding protein is a fusion protein of a peptide scaffold and of the said at least one CDR.

One or more sequences among the six CDR sequences described in the present invention can also be present on the various immunoglobulin protein scaffolding. In this case, the protein sequence makes it possible to recreate a peptide skeleton suitable for the correct folding of the grafted CDRs, enabling them to preserve their paratope antigen-recognition properties.

The person skilled in the art will be aware of means to select the type of protein scaffold for CDR grafting. More particularly, it is known that to be selected, such scaffolds must meet as many criteria as possible (Skerra A., J. Mol. Recogn., 2000, 13:167-187):

good phylogenetic conservation;
known three-dimensional structure (as determined by, for example, crystallography, NMR spectroscopy or any other technique known to a person skilled in the art);
small size;
few or no post-transcriptional modifications; and/or
easy to produce, express and purify.

Lastly, as described above, such peptide scaffolds comprise from one to six CDRs arising from the original antibody. Preferably, but not being a requirement, a person skilled in the art will select at least one CDR from the heavy chain, the latter being known to be primarily responsible for the specificity of the antibody. The selection of one or more relevant CDRs is obvious to a person skilled in the art, who will then choose suitable known techniques (Bes et al., FEBS letters 508, 2001, 67-74).

The present invention thus relates to an antibody, or a derived compound or functional fragment thereof, wherein the peptide scaffold is selected among proteins that are a) phylogenetically well preserved, b) of robust architecture, c) with a well-known 3-D molecular organization, d) of small size and/or e) comprising regions that can be modified by deletion and/or insertion without modifying stability properties.

According to a preferred embodiment, the said peptide scaffold is selected among i) scaffolds arising from fibronectin, preferentially fibronectin type 3 domain 10, lipocalin, anticalin, protein Z arising from domain B of protein A of *Staphylococcus aureus*, thioredoxin A or proteins with a repeated motif such as the "ankyrin repeat" (Kohl et al., PNAS, 2003, vol. 100, No. 4, 1700-1705), the "armadillo repeat", the "leucine-rich repeat" and the "tetratricopeptide repeat" or iii) protein inhibiters of neuronal NO synthase (PIN).

Another aspect of the invention relates to the functional fragments of the antibody described above.

More particularly, the invention targets an antibody, or a derived compound or functional fragment thereof, wherein the said functional fragment is selected among the fragments Fv, Fab, (Fab')$_2$, Fab', scFv, scFv-Fc and diabodies, or any fragment whose half-life has been increased such as PEGylated fragments.

By antigen-binding fragments (or "functional fragments": for the purposes of the application, these two terms are synonymous) of the antibody according to the invention, it is herein referred to, e.g., the fragments Fv, scFv (sc=single chain), Fab, F(ab')$_2$, Fab', scFv-Fc or diabodies, or any fragment whose half-life has been increased by chemical modification, such as the addition of polyalkylene glycol such as polyethylene glycol (PEGylation) (PEGylated fragments are referred to as Fv-PEG, scFv-PEG, Fab-PEG, F(ab')₂-PEG and Fab'-PEG), or by incorporation in a liposome, microspheres or PLGA In particular, the said fragments according to the invention contain at least one of the characteristic CDRs of the invention, such that they retain the binding activity and specificity, even partial, of the parent antibody.

Preferably, said antigen-binding fragments will comprise or include a partial sequence of the variable heavy or light chain of the antibody from which they are derived, said partial sequence being sufficient to retain the same binding specificity as the antibody from which it arises and sufficient affinity. The said affinity of the said fragment is preferably at least equal to 1/100, more preferably at least 1/10 of that of the antibody from which it arises.

Such an antigen-binding fragment contains at least five amino acids, preferably 6, 7, 8, 10, 15, 25, 50 or 100 consecutive amino acids of the sequence of the antibody from which it arises.

According to the present invention, antigen-binding fragments can be obtained from the antibodies of the invention by such methods as enzyme digestion, including pepsin or papain, and/or cleavage of the disulfide bridges by chemical reduction. The antibody fragments can be also obtained by recombinant genetics techniques or by peptide synthesis.

For clarity sake, table 2 below summarizes the various amino acid sequences corresponding to the antibody 427aB1 of the invention.

TABLE 2

(wherein Mu. = murine)

| Antibody | Heavy Chain | Light Chain | SEQ ID No. |
|---|---|---|---|
| 427aB1 | CDR-H1 | | 1 |
| | CDR-H2 | | 2 |
| | CDR-H3 | | 3 |
| | | CDR-L1 | 4 |
| | | CDR-L2 | 5 |
| | | CDR-L3 | 6 |
| | Mu. variable domain | | 7 |
| | | Mu. Variable domain | 8 |

According to another aspect, the invention relates to a murine hybridoma capable of secreting a monoclonal antibody according to the invention. Preferably, the said hybridoma is the hybridoma deposited at the CNCM, Institut Pasteur, Paris, France, on Jun. 25, 2008, under reference I-4018. The said hybridoma was obtained by fusing Balb/C immunized mice splenocytes with cells of the myeloma Sp 2/O—Ag 14 lines.

According to another preferred embodiment of the invention, the monoclonal antibody, herein referred to as 427aB1, or an antigen-binding fragment or derivative thereof, is secreted by the said hybridoma.

A novel aspect of the present invention relates to an isolated nucleic acid, characterized in that it is chosen from the following nucleic acids:

a) a nucleic acid, DNA or RNA, coding for an antibody or for a derived compound or functional fragment thereof, according to the invention;

b) a nucleic acid comprising a DNA sequence comprising a sequence selected from the group consisting of the sequences SEQ ID No. 9 to 14, or a sequence with at least 80%, preferably 85%, 90%, 95% and 98% identity after optimal alignment with the sequences SEQ ID No. 9 to 14;

c) a nucleic acid comprising a DNA sequence comprising the sequences SEQ ID No. 15 or 16, or a sequence with at least 80%, preferably 85%, 90%, 95% and 98% identity after optimal alignment with the sequences SEQ ID No. 15 or 16;

d) the RNA translated from the nucleic acids as defined in a), b) or c);

e) the complementary nucleic acids of the nucleic acids as defined in a), b) and c); and f) a nucleic acid of at least 18 nucleotides capable of hybridizing under conditions of high stringency with the sequences SEQ ID No. 15 or 16 or a sequence with at least 80%, preferably 85%, 90%, 95% and 98% identity after optimal alignment with sequences SEQ ID 15 or 16, or a complementary sequence thereof.

Table 3 below summarizes the various nucleotide sequences concerning the antibody 427aB1 of the invention.

TABLE 3

(wherein Mu. = murine)

| Antibody | Heavy Chain | Light Chain | SEQ ID No. |
|---|---|---|---|
| 427aB1 | CDR-H1 | | 9 |
| | CDR-H2 | | 10 |
| | CDR-H3 | | 11 |
| | | CDR-L1 | 12 |
| | | CDR-L2 | 13 |
| | | CDR-L3 | 14 |
| | Mu. variable domain | | 15 |
| | | Mu. Variable domain | 16 |

The terms "nucleic acid", "nucleic sequence", "nucleic acid sequence", "polynucleotide", "oligonucleotide", "polynucleotide sequence" and "nucleotide sequence", used interchangeably in the present description, mean a precise sequence of nucleotides, modified or not, defining a fragment or a region of a nucleic acid, containing unnatural nucleotides or not, and being either a double-strand DNA, a single-strand DNA or transcription products of said DNAs.

"Nucleic sequences exhibiting a percentage identity of at least 80%, preferably 85%, 90%, 95% and 98%, after optimal alignment with a preferred sequence" means nucleic sequences exhibiting, with respect to the reference nucleic sequence, certain modifications such as, in particular, a deletion, a truncation, an extension, a chimeric fusion and/or a substitution, notably punctual. Preferably, these are sequences which code for the same amino acid sequences as the reference sequence, this being related to the degeneration of the genetic code, or complementarity sequences that are likely to hybridize specifically with the reference sequences, preferably under highly stringent conditions, notably those defined below.

Hybridization under highly stringent conditions means that conditions related to temperature and ionic strength are selected in such a way that they allow hybridization to be maintained between two complementarity DNA fragments. On a purely illustrative basis, the highly stringent conditions of the hybridization step for the purpose of defining the polynucleotide fragments described above are advantageously as follows.

DNA-DNA or DNA-RNA hybridization is carried out in two steps: (1) prehybridization at 42° C. for three hours in phosphate buffer (20 mM, pH 7.5) containing 5×SSC (1×SSC corresponds to a solution of 0.15 M NaCl+0.015 M sodium citrate), 50% formamide, 7% sodium dodecyl sulfate (SDS), 10×Denhardt's, 5% dextran sulfate and 1% salmon sperm DNA; (2) primary hybridization for 20 hours at a temperature depending on the length of the probe (i.e.: 42° C. for a probe>100 nucleotides in length) followed by two 20-minute washings at 20° C. in 2×SSC+2% SDS, one 20-minute washing at 20° C. in 0.1×SSC+0.1% SDS. The last washing is carried out in 0.1×SSC+0.1% SDS for 30 minutes at 60° C. for a probe>100 nucleotides in length. The highly stringent hybridization conditions described above for a polynucleotide of defined size can be adapted by a person skilled in the art for longer or shorter oligonucleotides, according to the procedures described in Sambrook, et al. (Molecular cloning: a laboratory manual, Cold Spring Harbor Laboratory; 3rd edition, 2001).

The invention also relates to a vector comprising in the polynucleotide of the invention.

Specifically, the invention provides cloning and/or expression vectors that carry such a nucleotide sequence.

The vectors of the invention preferably contain elements allowing the expression of nucleotide sequences in a given host cell. In order to express the antibodies of the invention, the polynucleotides encoding said antibodies heavy and/or light chains are inserted into expression vectors such that the genes are operatively linked to transcriptional and translational sequences. "Operably linked" sequences include both expression control sequences that are contiguous with the gene of interest and expression control sequences that act in trans or at a distance to control the gene of interest. The term "expression control sequence" as used herein refers to polynucleotide sequences which are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i. e., Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences.

The term "vector", as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e. g., bacterial vectors having a bacterial origin of replication and episomal mammalian vectors). Other vectors (e. g., non-episomal mammalian vectors) can be integrated into the genome of a host cell upon introduction into the host cell, and thereby are replicated along with the host genome.

The vectors according to the invention may also contain a sequence allowing the stable maintenance of the said vectors in the host cell. It will be easily realized that such sequences, designated replication origins, vary according to the type of host cells. These various elements may be selected and optimized by a person skilled in the art according to the host cell used. For this purpose, the nucleotide sequences can be inserted in self-replicating vectors within the chosen host or be integrative vectors of the chosen host.

Such vectors are prepared by methods typically used by a person skilled in the art and the resulting clones can be introduced into a suitable host by standard methods such as lipofection, electroporation, heat shock or chemical methods.

The invention is also directed to host cells transformed by or comprising a vector as described in the present invention.

The host cell can be selected among prokaryotic or eukaryotic systems such as bacterial cells, for example, but also yeast cells or animal cells, notably mammal cells. Insect or plant cells can also be used.

The invention also relates to animals, other than man, or plants that contain a transformed cell according to the invention.

Another aspect of the invention relates to a method of producing an antibody according to the invention, an antigen-binding fragment or derivative, characterized in that said method comprises the steps of a) growing a host cell according to the invention in an appropriate medium under appropriate conditions; and b) recovering said antibody, or antigen-binding fragment or derivative thereof.

The resulting expressed antibody may then be purified from the culture medium or cell extracts. Soluble forms of the antibody of the invention can be recovered from the culture supernatant. It may then be purified by any method known in the art for purification of an immunoglobulin molecule, for example, by chromatography (e.g., ion exchange, affinity, particularly by Protein A affinity for Fc, and so on), centrifugation, differential solubility or by any other standard technique for the purification of proteins. Suitable methods of purification will be apparent to a person of ordinary skills in the art.

The polypeptides of the invention can also be prepared by chemical synthesis. Such methods of preparation are also within the scope of the invention. Several methods for chemical synthesis, such as solid-phase techniques (see notably Steward et al., 1984, Solid phase peptides synthesis, Pierce Chem. Company, Rockford, 111, 2nd ed.) or partial solid-phase techniques, by condensation of fragments or by conventional synthesis in solution, are known to the person skilled in the art. Polypeptides obtained by chemical synthesis and containing corresponding unnatural amino acids are also comprised in the invention. The antibodies, or the antigen-binding fragments or derivatives thereof, obtainable by the method of the invention are also comprised within the present invention.

As above mentioned, the antibody of the invention, or an antigen-binding fragment or derivative thereof, is capable of binding to CXCR4 as monomer and/or homodimer.

Surprisingly, the applicant has also demonstrated that said antibody, or an antigen-binding fragment or derivative thereof, does not bind significantly to CXCR4 as heterodimer. Preferably, the said antibody, or antigen-binding fragment or derivative does not bind to a CXCR4/CXCR2 heterodimer.

Antibodies of the prior art, such as 515H7, are known to be either capable of binding to CXCR4 as a monomer, homodimer or heterodimer (WO 2010/037831). In contrast, the antibody of the invention shows strong specificity with regards to the CXCR4 isoforms, since it is capable of discriminating between homo- and heterodimers. This property makes the antibody of the invention a preferred tool for differential screening and for example for characterizing a tumor.

By "CXCR4 as a monomer and/or a homodimer", or "monomeric/homodimeric CXCR4" (for the purposes of this application, these two terms are synonymous and are meant to be used interchangeably), it is herein referred to CXCR4 in monomeric form, i.e. not engaged in any physical interaction with any protein partner, and/or in homodimeric form, i.e. engaged in a complex with another molecule of CXCR4. The expression "CXCR4 as a monomer and/or a homodimer", or "monomeric/homodimeric CXCR4", is meant to specifically exclude CXCR4 heterodimers, i.e. dimers of CXCR4 with any other protein partner, except CXCR4 itself. In particular, the expression "CXCR4 as a monomer and/or a homodimer", or "monomeric/homodimeric CXCR4", specifically excludes CXCR4/CXCR2 heterodimers.

The invention thus relates to the antibody described above, or an antigen-binding fragment or derivative thereof, for use in in vitro or ex vivo diagnosis and/or prognosis of an oncogenic disorder associated with expression of CXCR4.

The invention thus relates to a method of in vitro or ex vivo diagnosing and/or prognosing an oncogenic disorder associated with expression of CXCR4, comprising the step of testing the binding of an antibody of the invention, or a fragment or a derivative thereof, to CXCR4.

In a preferred embodiment, said oncogenic disorder consists of an oncogenic disorder associated with expression of CXCR4 monomer and/or homodimer.

"Diagnosing" a disease as used herein refers to the process of identifying or detecting the presence of a pathological hyperproliferative oncogenic disorder associated with or mediated by expression of monomeric/homodimeric CXCR4, monitoring the progression of the disease, and identifying or detecting cells or samples that are indicative of a disorder associated with the expression of CXCR4 monomer and/or homodimer.

"Prognosis" as used herein means the likelihood of recovery from a disease or the prediction of the probable development or outcome of a disease. For example, if a sample from a subject is negative for staining with the antibody of the invention, then the "prognosis" for that subject is better than if the sample is positive for monomeric/homodimeric CXCR4 staining Samples may be scored for monomeric/homodimeric CXCR4 expression levels on an appropriate scale as it will be more detailed hereinafter.

The binding of the antibody of the invention, or fragment or derivative thereof, to CXCR4, including the CXCR4 monomers, the CXCR4/CXCR4 homodimers, and CXCR4/CXCR2 heterodimers, can be tested in a number of ways known to the person skilled in the art. One such method, namely a BRET assay, is detailed described in WO 2010/037831. The 515H7 antibody can be conveniently used as positive control for the binding assay.

The antibody of the invention, or an antigen-binding fragment or derivative thereof, may be a murine antibody. However, a chimeric or humanized version of such an antibody should be also considered as part of the scope of the present invention, since such antibodies would comprise the CDRs of the antibody herein described.

Importantly, the antibody, or antigen-binding fragment or derivative, of the invention does not block 515H7 binding to CXCR4. It is thus possible to use the antibody of the invention during a treatment with the 515H7 antibody without interfering with the said treatment, since these two antibodies do not compete for CXCR4. The antibody of the invention is thus a critical tool for monitoring, e.g. by in vivo imaging of the tumor, the efficacy of a therapy based on the said antibody 515H7.

In a more preferred embodiment of the invention, the said antibody, or antigen-binding fragment or derivative, does not have any in vivo anti-tumoral activity.

This property is of great interest in the diagnostic application as it will allow the use of an antibody for screening patient, or following the progress of a treatment using an agent which will not have any impact or consequence on the patient. This property makes the antibody 427aB1 a preferred tool for screening patient to be treated as it will have no impact for the patient. As it will be recognized by the person skilled in that art, the applicant has provided a really novel and inventive antibody by generating an antibody able to recognize CXCR4, both as a monomer and as a homodimer, with no anti-tumoral activity in vivo.

The antibody can be present in the form of an immunoconjugate or of a labeled antibody as to obtain a detectable and/or quantifiable signal. When used with suitable labels or other appropriate detectable biomolecule or chemicals, the antibody of the invention is particularly useful for in vitro and in vivo diagnosis and prognosis applications.

Labels for use in immunoassays are generally known to those skilled in the art. Such labels include, inter alia, enzymes, radioisotopes, and fluorescent, luminescent and chromogenic substances, including colored particles such as colloidal gold or latex beads. Various types of labels and methods of conjugating the labels to the antibodies of the invention are well known to those skilled in the art, such as the ones set forth below.

As used herein, the term "an oncogenic disorder associated with expression of CXCR4 as monomer and/or homodimer" is intended to refer to diseases and other disorders in which the presence of high levels of monomeric/homodimeric CXCR4 (aberrant) in a subject suffering from the disorder has been shown to be, or is suspected of being, either responsible for the pathophysiology of the disorder or a factor that contributes to a worsening of the disorder. Such disorders may be evidenced, for example, by an increase in the levels of CXCR4, preferably CXCR4 as monomer and/or homodimer on the cell surface in the affected cells or tissues of a subject suffering from the disorder. The increase in monomeric and/or homodimeric CXCR4 levels may be detected, for example, using the antibody 427aB1 of the invention.

In certain embodiments, "increased expression" as it relates to CXCR4 as monomer and/or homodimer refers to protein or gene expression levels that demonstrate a statistically significant increase in expression (as measured by RNA expression or protein expression) relative to a control.

In another embodiment, the invention relates to a method for detecting the presence of a monomeric/homodimeric CXCR4-expressing tumor in a subject, said method comprising the steps of: a) administering the antibody of the invention, or an antigen-binding fragment or derivative thereof, to the subject; and b) detecting binding of said antibody, wherein said binding indicates the presence of the tumor.

A preferred aspect of the invention is a method for detecting ex vivo the presence of a monomeric/homodimeric CXCR4-expressing tumor in a subject, wherein said process comprises the steps of:

(a) contacting a biological sample from the said subject with an antibody of the invention, or an antigen-binding fragment or derivative thereof, and (b) detecting the binding of said antibody with the biological sample.

The binding of the antibody of the invention may be detected by various assays available to the skilled artisan.

Although any suitable means for carrying out the assays are included within the invention, it can be mentioned in particular FACS, ELISA, western-blot and IHC.

In another embodiment, the invention relates to a method of detecting the location of a monomeric/homodimeric CXCR4-expressing tumor in a subject, comprising the steps of:

a) administering the antibody according to the invention, or an antigen-binding fragment or derivative thereof, to the said subject; and b) detecting binding of said antibody, wherein said binding indicates the presence of the tumor.

As for the detection of the presence of a expressing tumor, many techniques known by the man skilled in the art can be used. Nevertheless, preferred means are the IHC or the FACS.

Another aspect of the invention relates to a method for determining in vitro or ex vivo the percentage of cells expressing CXCR4 as monomer and/or homodimer in a tumor from a subject, the said method comprising the steps of:

(a) contacting a biological sample from the subject with an antibody according to the invention or an antigen-binding fragment or derivative thereof, and (b) quantifying the percentage of cells expressing CXCR4 as monomer and/or homodimer in the said biological sample.

Yet another aspect of the invention relates to a method for determining in vitro or ex vivo the expression level of monomeric/homodimeric CXCR4 in a tumor from a subject, the said method comprising the steps of:

(a) contacting a biological sample from the subject with an antibody according the invention, or an antigen-binding fragment or derivative thereof, and (b) quantifying the level of binding of the said antibody, or antigen-binding fragment or derivative thereof, to monomeric/homodimeric CXCR4 in the said biological sample.

The level of binding of the said antibody to the monomeric/homodimeric CXCR4 expression level can be measured by immunohistochemistry (IHC) or FACS, preferably by IHC.

Once a determination is made of the amount of CXCR4 as a monomer and/or homodimer present in the test sample, the results can be compared with those of control samples, which are obtained in a manner similar to the test samples but from individuals that do not have a hyperproliferative oncogenic disorder associated with expression of CXCR4 as monomer and/or homodimer. If the level of the monomeric/homodimeric CXCR4 is significantly elevated in the test sample, it may be concluded that there is an increased likelihood of the subject from which it was derived has or will develop said disorder.

With regards to the development of targeted antitumor therapy, the diagnosis with immunohistological techniques gives in situ information on the receptor expression level and thus enables to select patients susceptible to be treated following the expression level of receptors needed for such a treatment.

Stage determination has potential prognosis value and provides criteria for designing optimal therapy. Simpson et al., J. Clin. Oncology 18:2059 (2000). For example, treatment selection for solid tumors is based on tumor staging, which is usually performed using the Tumor/Node/Metastasis (TNM) test from the American Joint Committee on Cancer (AJCC). It is commonly acknowledged that, while this test and staging system provides some valuable information concerning the stage at which solid cancer has been diagnosed in the patient, it is imprecise and insufficient. In particular, it fails to identify the earliest stages of tumor progression.

The invention thus relates to a method for determining in vitro or ex vivo the scoring of a tumor from a subject, said method comprising the steps of:

(a) contacting a biological sample from the subject with an antibody of the invention, or an antigen-binding fragment or derivative thereof, (b) quantifying the level of binding of the said antibody, or antigen-binding fragment or derivative thereof, to monomeric/homodimeric CXCR4 in the said biological sample; and (c) scoring the tumor by comparing the quantified level of binding of the said antibody, or antigen-binding fragment or derivative thereof, from the subject to an appropriate scale.

In a preferred embodiment, the said antibody for diagnosis is capable of binding the targeted receptor when tissue samples are, formalin fixed-, formol substituted fixed-, such as Glyco-fixx fixed-, paraffin embedded and/or frozen.

Preferably, the monomeric/homodimeric CXCR4 expression level is measured by immunohistochemistry (IHC) or FACS, more preferably by IHC.

Any conventional hazard analysis method may be used to estimate the prognostic value of CXCR4 as monomer and/or homodimer. Representative analysis methods include Cox regression analysis, which is a semiparametric method for modeling survival or time-to-event data in the presence of censored cases (Hosmer and Lemeshow, 1999; Cox, 1972). In contrast to other survival analyses, e.g. Life Tables or Kaplan-Meyer, Cox allows the inclusion of predictor variables (covariates) in the models. Using conventional analysis method, e.g., Cox one may be able to test hypotheses regarding the correlation of monomeric/homodimeric CXCR4-expression status of in a primary tumor to time-to-onset of either disease relapse (disease-free survival time, or time to metastatic disease), or time to death from the disease (overall survival time). Cox regression analysis is also known as Cox proportional hazard analysis. This method is standard for testing the prognostic value of a tumor marker on patient survival time. When used in multivariate mode, the effect of several covariates are tested in parallel so that individual covariates that have independent prognostic value can be identified, i.e. the most useful markers. The term negative or positive "monomeric/homodimeric CXCR4 status" is also referred to herein as [monomeric/homodimeric CXCR4 (−)] or [monomeric/homodimeric CXCR4 (+)].

A sample may be "scored" during the diagnosis or monitoring of cancer. In its simplest form, scoring may be categorical negative or positive as judged by visual examination of samples by immunohistochemistry. More quantitative scoring involves judging the two parameters intensity of staining and the proportion of stained ("positive") cells that are sampled.

"Monomeric/homodimeric CXCR4 status" herein refers to the classification of tumor as positive for CXCR4 as a monomer and/or homodimer [monomeric/homodimeric CXCR4 (+)] or negative CXCR4 as a monomer and/or homodimer [monomeric/homodimeric CXCR4 (−)], based on the determination of the expression level of the monomeric/homodimeric CXCR4. The expression of CXCR4 can be detected and measured by any suitable method available to the person of skills in the art, such as immunohistochemistry (IHC) or FACS.

In an embodiment of the invention, to ensure standardization, samples may be scored for monomeric/homodimeric CXCR4 expression levels on different scales, most of them being based on an assessment of the intensity of the reaction product and the percentage of positive cells (Payne et al., Predictive markers in breast cancer—the present, Histopathology 2008, 52, 82-90).

In a more preferred embodiment, the said scoring comprises using an appropriate scale based on two parameters which are the intensity of the staining and the percentage of positive cells.

As a first example, based on the teaching from the Quick Allred scoring for IHC assessment of oestrogen receptor and progesterone receptor, samples may be scored for monomeric/homodimeric CXCR expression levels on a global scale from 0 to 8 combining scores for intensity of reactivity and for the proportion of cells stained (Harvey J M, Clarck G M, Osborne C K, Allred DC; J. Clin. Oncol. 1999; 17; 1474-1481). More particularly, the first criteria of intensity of reactivity is scored on a scale from 0 to 3, 0 corresponding to "No reactivity" and 3 corresponding to "Strong reactivity". The second criteria of proportion reactive is scored on a scale from 0 to 5, 0 corresponding to "No reactivity" and 5 to "67-100% proportion reactive". The intensity of reactivity score and the proportion reactive score are then summed to produce total score of 0 through 8.

A total score of 0-2 is regarded as negative while a total score of 3-8 is regarded as positive.

According to this scale, the terms negative or positive "monomeric/homodimeric CXCR4 status" of tumors used in the present description refers to levels of expression of CXCR4 as a monomer and/or homodimer that correspond to scores 0-2 or 3-8 on the Allred scale, respectively.

Table 4 hereinafter illustrates the guidelines for interpreting IHC results according to Allred method.

TABLE 4

| Intensity of immunoreactivity | Score 1 | Proportion reactive | Score 2 |
|---|---|---|---|
| No reactivity | 0 | No reactivity | 0 |
| Weak reactivity | 1 | <1% | 1 |
| Moderate reactivity | 2 | 1-10% | 2 |
| Strong reactivity | 3 | 11-33% | 3 |
| — | | 34-66% | 4 |
| — | | 67-100% | 5 |

| Total Score (Score 1 + Score 2) | Interpretation |
|---|---|
| 0-2 | Negative |
| 3-8 | Positive |

In a preferred embodiment, the process according to the invention refers to an appropriate scale which is a scale of 0 to 8 wherein no reactivity is scored 0, and a strong reactivity in a proportion of 67-100% reactive is scored 8.

In another embodiment, it is provided a method of determining in vitro or ex vivo the status of a tumor from a subject, the said method comprising the steps of:
(a) scoring a tumor from a subject according to the Allred scale; and
(b) determining that the status of the tumor is [monomeric/homodimeric CXCR4(+)] with an Allred score of 3 to 8; or
(c) determining that the status of the tumor is [monomeric/homodimeric CXCR4(−)] with an Allred score of 0 to 2.

In a particular aspect of the invention, a tumor is [monomeric/homodimeric CXCR4 (+)] with an Allred score of 3.

In a particular aspect of the invention, a tumor is [monomeric/homodimeric CXCR4 (+)] with an Allred score of 4.

In a particular aspect of the invention, a tumor is [monomeric/homodimeric CXCR4 (+)] with an Allred score of 5.

In a particular aspect of the invention, a tumor is [monomeric/homodimeric CXCR4 (+)] with an Allred score of 6.

In a particular aspect of the invention, a tumor is [monomeric/homodimeric CXCR4 (+)] with an Allred score of 7.

In a particular aspect of the invention, a tumor is [monomeric/homodimeric CXCR4 (+)] with an Allred score of 8.

In another particular aspect of the invention, a tumor is [monomeric/homodimeric CXCR4 (+)] with an Allred score of 3 to 8.

As a second example, based on the teaching from the conventional scoring for IHC assessment of HER-2 receptor for example, samples may be scored for monomeric/homodimeric CXCR4 expression levels on a somewhat simpler scoring method, said scoring method integrating the intensity of staining (preferentially membranous staining) and the proportion of cells that display staining into a combined scale from 0 to 3+.

In this scale, referred as the simplified scale, 0 and 1+ are negative whereas 2+ and 3+ represents positive staining Nevertheless, scores 1+-3+ can be recoded as positive because each positive score may be associated with significantly higher risk for relapse and fatal disease when compared to score 0 (negative), but increasing intensity among the positive scores may provide additional risk reduction.

Generally speaking, the terms negative or positive "monomeric/homodimeric CXCR4 status" of tumors used in the present description refers to levels of expression of CXCR4 as monomer and/or homodimer that correspond to scores 0-1+ or 2+-3+ on the simplified scale, respectively. Only complete circumferential membranous reactivity of the invasive tumor should be considered and often resembled a "chicken wire" appearance. Under current guidelines, samples scored as borderline (score of 2+ or 3+) for CXCR4 as monomer and/or homodimer are required to undergo further assessment. The IHC analysis should be rejected, and either repeated or tested by FISH or any other method if, as non limitative example, controls are not as expected, artifacts involve most of the sample and the sample has strong membranous positivity of normal breast ducts (internal controls) suggesting excessive antigen retrieval.

For more clarity, table 5 hereinafter summarizes these parameters.

TABLE 5

| CXCR4 as monomer and/or homodimer status | IHC description |
|---|---|
| 0 | No reactivity or membranous reactivity in less than 10% of tumour cells. |
| 1+ | Faint/barely perceptible membranous reactivity is detected in more than 10% of tumour cells. The cells are immunoreactive only in part of the membrane. |
| 2+ | Weak to moderate complete membranous reactivity is seen in more than 10% of tumour cells. |
| 3+ | Strong complete reactivity is seen in more than 10% of tumour cells. |

In a preferred embodiment, the process according to the invention refers to an appropriate scale which is a scale of 0 to 3+ wherein no membranous reactivity of tumor cells is scored 0, and strong complete reactivity in more than 10% of tumor cells is scored 3+.

In more details, as above described, said appropriate scale is a scale of 0 to 3 wherein no membranous reactivity of tumor cells is scored 0; faint perceptible membranous reactivity in more than 10% of tumor cells is scored 1+; weak to moderate complete membranous reactivity in more than 10% of tumor cells is scored 2+; and strong complete reactivity in more than 10% of tumor cells is scored 3+.

Therefore, another embodiment of the invention provides a process of determining in vitro or ex vivo the status of a tumor from a subject, the said method comprising the steps of:

(a) scoring a tumor from a subject according to the simplified scale as above described; and (b) determining that the status of the tumor is [monomeric/homodimeric CXCR4(+)] with a score of 2+ or 3+; or (c) determining that the status of the tumor is [monomeric/homodimeric CXCR4(−)] with a score of 0 or 1+.

In a particular aspect of the invention, a tumor is [monomeric/homodimeric CXCR4 (+)] with a score of 2+.

In a particular aspect of the invention, a tumor is [monomeric/homodimeric CXCR4 (+)] with a score of 3+.

In another particular aspect of the invention, a tumor is [monomeric/homodimeric CXCR4 (+)] with a score of 2+ or 3+.

The results of a test or assay according to the invention can be presented in any of a variety of formats.

The results can be displayed qualitatively. For example, the test report may indicate only whether or not a particular polypeptide was detected, perhaps also with an indication of the limits of detection. The results may be displayed as semi-quantitative. For example, various ranges may be defined, and the ranges may be assigned a score (e.g., 0 to 3+ or 0 to 8 depending on the used scale) that provides a certain degree of quantitative information. Such a score may reflect various factors, e.g., the number of cells in which CXCR4 as monomer and/or homodimer is detected, the intensity of the signal (which may indicate the level of expression of monomeric/homodimeric CXCR4 or CXCR4 bearing cells), etc. The results may be displayed in a quantitative way, e.g., as a percentage of cells in which the polypeptide (CXCR4) is detected, as a protein concentration, etc.

As will be appreciated by one of ordinary skills in the art, the type of output provided by a test will vary depending upon the technical limitations of the test and the biological significance associated with detection of the polypeptide. For example, in the case of certain polypeptides, a purely qualitative output (e.g., whether or not the polypeptide is detected at a certain detection level) provides significant information. In other cases a more quantitative output (e.g., a ratio of the level of expression of the polypeptide in the sample being tested versus the normal level) is necessary.

The invention also relates to a method for determining whether an oncogenic disorder is susceptible to treatment with a CXCR4 antagonist, the said method comprising the steps of:

(a) determining in vitro or ex vivo the status of a tumor of a subject as above described, and (b) determining that, if the status is [monomeric/homodimeric CXCR4(+)], the oncogenic disorder is susceptible to treatment with a CXCR4 antagonist.

In a preferred embodiment, the CXCR4 antagonist is an anti-CXCR4 antibody, or fragment or derivative thereof, as described above.

In another aspect, the invention relates to a method of diagnosing a pathological hyperproliferative oncogenic disorder or a susceptibility to a pathological condition associated with expression of monomeric/homodimeric CXCR4 in a subject, said subject comprising (a) determining the presence or absence of monomeric/homodimeric CXCR4 in a sample, and (b) diagnosing a pathological condition or susceptibility to a pathological condition based on the presence or absence of said CXCR4 as monomer and/or homodimer.

In the methods of the invention, the detection of monomeric/homodimeric CXCR4-expressing cells or an increase in the levels of monomeric/homodimeric CXCR4 is generally indicative of a patient with or suspected of presenting with a monomeric/homodimeric CXCR4-mediated disorder.

The invention thus provides a method for predicting the risk of an individual to develop a cancer, said method comprising detecting the expression level of monomeric/homodimeric CXCR4 in a biological sample, wherein a high monomeric/homodimeric CXCR4 expression level indicates a high risk of developing a cancer.

It has been observed that CXCR4 expression is significantly associated with progressed tumor stages. in several types of cancers (Schimanski et al., *J Clin Oncol*, ASCO Annual Meeting Proceedings Part I., 24(18S): 14018, 2006; Lee et al., *Int J Oncol.*, 34(2):473-480, 2009; Pagano, Tesi di dottorato, Università degli Studi di Napoli Federico II, 2008).

Thus the invention also relates to a method for evaluating tumor aggressiveness. "Tumor aggressiveness" as used herein refers to a tumor quickly growing and tending to spread rapidly. In one embodiment, the said method comprises the step of:

(a) determining the level of monomeric/homodimeric CXCR4 expressed by cells in a tumor sample of an individual, and (b) determining the level of monomeric/homodimeric CXCR4 expressed in an equivalent tissue sample taken from the same individual at a later time, (c) calculating the ratio between the expression level obtained in state (a) and the expression level obtained in step (b), wherein the ratio of monomeric/homodimeric CXCR4 expression in the tumor sample over time provides information on the risks of cancer progression.

In a preferred embodiment, a ratio of the level obtained in step (a) to the level obtained in step (b) smaller than 1 indicates aggressiveness. In another embodiment, a ratio greater than or equal to 1 indicates non aggressiveness.

Another aspect of the invention is the monitoring of the expression of CXCR4 as a monomer and/or homodimer in response to a monomeric/homodimeric CXCR4-targeted therapy. Such a monitoring can very useful when the said therapy triggers the downregulation and/or the degradation of monomeric/homodimeric CXCR4.

In particular, monitoring monomeric/homodimeric CXCR4 expression on the cell surface could be a critical tool to evaluate the efficacy of the treatment during clinical trials and "personalized" therapies.

The application thus provides methods for determining the appropriate therapeutic regimen for a subject.

An increase or a decrease in the level of monomeric/homodimeric CXCR4 is indicative of the evolution of a cancer associated with monomeric/homodimeric CXCR4. Thus, by measuring an increase in the number of cells expressing monomeric/homodimeric CXCR4 or changes in the concentration of monomeric/homodimeric CXCR4 present in various tissues or cells, it is possible to determine whether a particular therapeutic regimen aimed at ameliorating a malignancy associated with CXCR4 is effective.

Therefore, the present invention is also directed to a method for determining the efficacy of a therapeutic regime designed to alleviate an oncogenic disorder associated with monomeric/homodimeric CXCR4 in a subject suffering from said disorder, comprising steps of:

(a) determining a first expression level of monomeric/homodimeric CXCR4 in a biological sample extracted from the subject at a first time point;

(b) determining a second expression level of monomeric/homodimeric CXCR4 in a biological sample extracted from the subject at a second later time point;

(c) determining the ratio of the level obtained in (a) to the level obtained in (b); and (d) determining that the efficacy of said therapeutic regime is high when the ratio of step (c) is higher than 1; or (e) determining that the efficacy of said therapeutic regime is low when the ratio of step (c) is inferior or equal to 1.

In a preferred embodiment, the therapeutic regime designed to alleviate an oncogenic disorder associated with monomeric/homodimeric CXCR4 in a subject suffering from said disorder includes the administration of a CXCR4 inhibitor to the said subject.

Another preferred embodiment of the invention provides a method for selecting a cancer patient predicted to benefit or not from the administration of a therapeutic amount of a CXCR4 inhibitor, the said method comprising the steps of:

(a) determining the expression level of monomeric/homodimeric CXCR4 in the said patient;

(b) determining a reference expression level of monomeric/homodimeric CXCR4 from a healthy individual;

(c) determining the ratio between the level obtained in step (a) and the reference level obtained in step (b), and (d) selecting the patient as being predicted to benefit from the administration of a therapeutic amount of a CXCR4 inhibitor, if the ratio of step (c) is greater than 1; or (e) selecting the patient as being not predicted to benefit from the administration of a therapeutic amount of a CXCR4 inhibitor, if the ratio of step (c) is equal to or smaller than 1.

In the sense of the present specification, the expression "CXCR4 inhibitor" or "CXCR4 inhibitor compound" refer to any compound or molecule capable of binding to CXCR4 and to inhibit the binding of the CXCR4 ligand. As non limitative example, CXCR4 inhibitors include AMD3100 and AMD3465. Other CXCR4 inhibitors that may be used include but are not limited to CTCE-0214; CTCE-9908; CP-1221 (linear peptides, cyclic peptides, natural amino-acids, unnatural amino acids, and peptidomimetic compounds); T140 and analogs; 4F-benzoyl-TN24003; KRH-1120; KRH-1636; KRH-2731; polyphemusin analogue; ALX40-4C; or those described in WO 01/85196; WO 99/50461; WO 01/94420; WO 03/090512, each of which is incorporated by reference herein.

In a preferred embodiment, the said inhibitors are monoclonal antibodies such as those described in patents WO2008/060367 and WO2009/140124.

In the most preferred embodiment, the said CXCR4 inhibitor is the monoclonal antibody 515H7 (WO2010/037831).

It is also an object of the invention to provide an in vivo method of imaging an oncogenic disorder associated with expression of CXCR4 as monomer and/or homodimer. Such a method is useful for localizing in vivo the tumor, as well as monitoring its invasiveness. Likewise, the method is useful for monitoring the progression and/or the response to treatment in patients previously diagnosed with a monomeric/homodimeric CXCR-mediated cancer.

In a first aspect, the invention provides an in vivo imaging reagent, the said reagent comprising an antibody according to the invention, or an antigen-binding fragment or derivative thereof, the said antibody or fragment or derivative thereof being preferably labeled, more preferably radiolabeled. The said reagent can be administered to a patient suffering from a patient monomeric/homodimeric CXCR4-mediated cancer in combination with a pharmaceutically effective carrier. The present invention also contemplates the use of the said reagent in medical imaging of a patient suffering from a monomeric/homodimeric CXCR4-mediated cancer. The method of the invention comprises the steps of:

(a) administering to the said patient an imaging-effective amount of an imaging reagent and (b) detecting the said reagent.

In a first embodiment, the imaging agent comprises a targeting moiety and an active moiety.

As used herein, the term "targeting moiety" refers to an agent that specifically recognizes and binds monomeric/homodimeric CXCR4 on the cell surface. In a particular embodiment, the targeting moiety is an antibody or a fragment or a derivative thereof which binds specifically to monomeric/homodimeric CXCR4. Specifically, the targeting moiety is an antibody or fragment or derivative thereof as described above. An "active moiety" as used herein is an agent which permits in vivo detection of the said imaging reagent. The active moiety according to the invention includes in particular radio-elements such as Technetium-99m (99mTc), Copper-67 (Cu-67), Scandium-47 (Sc-47), Luthetium-77 (Lu-177) copper-64 (Cu-64), Yttrium-86 (Y-86) or Iodine-124 (I-124).

The imaging agent is administered in an amount effective for diagnostic use in a mammal such as a human and the localization and accumulation of the imaging agent is then detected. The localization and accumulation of the imaging agent may be detected by radionucleide imaging, radioscintigraphy, nuclear magnetic resonance imaging, computed tomography, positron emission tomography, computerized axial tomography, X-ray or magnetic resonance imaging method, fluorescence detection, and chemiluminescent detection.

A "biological sample" may be any sample that may be taken from a subject. Such a sample must allow for the determination of the expression levels of the biomarker of the invention. The nature of the sample will thus be dependent upon the nature of the tumor. Preferred biological samples for the determination of the said biomarkers expression level by detection of the activated Akt and/or Erk proteins include samples such as a blood sample, a plasma sample, or a lymph sample, if the cancer is a liquid tumor. By "liquid tumor", it is herein referred to tumors of the blood or bone marrow, i.e. hematologic malignancies such as leukemia and multiple myeloma. Preferably, the biological sample is a blood sample. Indeed, such a blood sample may be obtained by a completely harmless blood collection from the patient and thus allows for a non-invasive diagnosis of a CXCR4-inhibitor responding or non-responding phenotype.

A "biological sample" as used herein also includes a solid cancer sample of the patient to be tested, when the cancer is a solid cancer. Such solid cancer sample allows the skilled person to perform any type of measurement of the level of the biomarker of the invention. In some cases, the methods according to the invention may further comprise a preliminary step of taking a solid cancer sample from the patient. By a "solid cancer sample", it is referred to a tumor tissue sample. Even in a cancerous patient, the tissue which is the site of the tumor still comprises non tumor healthy tissue.

The "cancer sample" should thus be limited to tumor tissue taken from the patient. Said "cancer sample" may be a biopsy sample or a sample taken from a surgical resection therapy.

According to one aspect, the sample from the patient is a cancer cell or a cancer tissue.

This sample may be taken and if necessary prepared according to methods known to a person skilled in the art.

The cancer cell or cancer tissue in the present invention is not particularly limited.

As used herein, the term "cancer" refers to or describes the physiological condition in mammals that is typically characterized by unregulated cell proliferation. The terms "cancer" and "cancerous" as used herein are meant to encompass all stages of the disease. Thus, a "cancer" as used herein may include both benign and malignant tumors. Examples of cancer include but are not limited to, carcinoma, lymphoma, blastoma, sarcoma, and leukemia or lymphoid malignancies. More specifically, a cancer according to the present invention is selected from the group comprising squamous cell cancer (e.g., epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer and gastrointestinal stromal cancer, pancreatic cancer, glioblastoma, cervical cancer, ovarian cancer, liver cancer, bladder cancer, cancer of the urinary tract, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, melanoma, superficial spreading melanoma, lentigo maligna melanoma, acral lentiginous melanomas, nodular melanomas, multiple myeloma and B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); hairy cell leukemia; chronic myeloblastic leukemia (CML); Acute Myeloblastic Leukemia (AML); and post-transplant lymphoproliferative disorder (PTLD), as well as abnormal vascular proliferation associated with phakomatoses, edema (such as that associated with brain tumors), Meigs' syndrome, brain, as well as head and neck cancer, and associated metastases.

In a preferred embodiment, said cancer is selected among prostate cancer, osteosarcoma, lung cancer, breast cancer, endometrial cancer, leukemia, lymphoma, multiple myeloma, ovarian cancer, pancreatic cancer and colon cancer. In a more preferred embodiment, said cancer comprises lymphoma cell, leukemia cell or multiple myeloma cell.

The expression level of CXCR4 as monomer and/or homodimer is advantageously compared or measured in relation to levels in a control cell or sample also referred to as a "reference level" or "reference expression level". "Reference level", "reference expression level", "control level" and "control" are used interchangeably in the specification. As used herein, a "control level" means a separate baseline level measured in a comparable control cell, which is generally disease or cancer free. It may be from the same individual or from another individual who is normal or does not present with the same disease from which the diseased or test sample is obtained. Within the context of the present invention, the term "reference level" refers to a "control level" of expression of monomeric/homodimeric CXCR4 used to evaluate a test level of expression of monomeric/homodimeric CXCR4 in a cancer cell-containing sample of a patient.

For example, when the level of CXCR4 as monomer and/or homodimer in the biological sample of a patient is higher than the reference level of CXCR4 as monomer and/or homodimer, the cells will be considered to have a high level of expression, or overexpression, of CXCR4 as monomer and/or homodimer.

The reference level can be determined by a plurality of methods. Expression levels may thus define the number of monomeric/homodimeric CXCR4 expressing cells. Alternatively, the expression levels may define the level of expression of the said monomeric/homodimeric CXCR4, independently of the number of cells expressing monomeric/homodimeric CXCR4.

Thus the reference level for each patient can be prescribed by a reference ratio of monomeric/homodimeric CXCR4, wherein the reference ratio can be determined by any of the methods for determining the reference levels described herein.

For example, the control may be a predetermined value, which can take a variety of forms. It can be a single cut-off value, such as a median or mean. The "reference level" can be a single number, equally applicable to every patient individually, or the reference level can vary, according to specific subpopulations of patients. Thus, for example, older men might have a different reference level than younger men for the same cancer, and women might have a different reference level than men for the same cancer. Alternatively, the "reference level" can be determined by measuring the level of expression of CXCR4 as monomer and/or homodimer in non-oncogenic cancer cells from the same tissue as the tissue of the neoplastic cells to be tested. As well, the "reference level" might be a certain ratio of CXCR4 as monomer and/or homodimer in the neoplastic cells of a patient relative to the CXCR4 as monomer and/or homodimer levels in non-tumor cells within the same patient. The "reference level" can also be a level of CXCR4 as monomer and/or homodimer of in vitro cultured cells, which can be manipulated to simulate tumor cells, or can be manipulated in any other manner which yields expression levels which accurately determine the reference level. On the other hand, the "reference level" can be established based upon comparative groups, such as in groups not having elevated monomeric/homodimeric CXCR4 levels and groups having elevated monomeric/homodimeric CXCR4 levels. Another example of comparative groups would be groups having a particular disease, condition or symptoms and groups without the disease. The predetermined value can be arranged, for example, where a tested population is divided equally (or unequally) into groups, such as a low-risk group, a medium-risk group and a high-risk group.

The reference level can also be determined by comparison of the level of CXCR4 as monomer and/or homodimer in populations of patients having the same cancer. This can be accomplished, for example, by histogram analysis, in which an entire cohort of patients are graphically presented, wherein a first axis represents the level of CXCR4 as monomer and/or homodimer, and a second axis represents the number of patients in the cohort whose tumor cells express CXCR4 as monomer and/or homodimer at a given level. Two or more separate groups of patients can be determined by identification of subsets populations of the cohort which have the same or similar levels of CXCR4 as monomer and/or homodimer. Determination of the reference level can then be made based on a level which best distinguishes these separate groups. A reference level also can represent the levels of two or more markers, one of which is monomeric/homodimeric CXCR4. Two or more markers can be represented, for example, by a ratio of values for levels of each marker.

Likewise, an apparently healthy population will have a different 'normal' range than will have a population which is known to have a condition associated with expression of CXCR4 as monomer and/or homodimer. Accordingly, the predetermined value selected may take into account the category in which an individual falls. Appropriate ranges and categories can be selected with no more than routine experimentation by those of ordinary skill in the art. By "elevated" "increased" it is meant high relative to a selected control. Typically the control will be based on apparently healthy normal individuals in an appropriate age bracket.

It will also be understood that the controls according to the invention may be, in addition to predetermined values, samples of materials tested in parallel with the experimental materials. Examples include tissue or cells obtained at the same time from the same subject, for example, parts of a single biopsy, or parts of a single cell sample from the subject.

In another embodiment, the invention relates to a pharmaceutical composition for in vivo imaging of an oncogenic disorder associated with expression of CXCR4 as monomer and/or homodimer, said composition comprising the monoclonal antibody of the invention, or antigen-binding fragment or derivative thereof, said antibody or fragment of derivative thereof being labeled and capable of binding CXCR4 as a monomer and/or a homodimer in vivo; as well as a pharmaceutically acceptable carrier. In another aspect, the present invention provides a kit useful for the methods described above, said kit comprising the antibody of the invention.

Packaged materials comprising a combination of reagents in predetermined amounts with instructions for performing the diagnostic assay, e.g. kits, are also within the scope of the invention. The kit contains the antibodies for detection and quantification of monomeric/homodimeric CXCR4 in vitro, e.g. in an ELISA or a Western blot. The antibody of the present invention can be provided in a kit for detection and quantification of monomeric/homodimeric CXCR4 in vitro, e.g. in an ELISA or a Western blot. Where the antibody is labeled with an enzyme, the kit will include substrates and cofactors required by the enzyme (e.g., a substrate precursor which provides the detectable chromophore or fluorophore). In addition, other additives may be included such as stabilizers, buffers (e.g., a block buffer or lysis buffer) and the like. Such a kit may comprise a receptacle being compartmentalized to receive one or more containers such as vials, tubes and the like, such containers holding separate elements of the invention. For example, one container may contain a first antibody bound to an insoluble or partly soluble carrier. A second container may contain soluble, detectably-labeled second antibody, in lyophilized form or in solution. The receptacle may also contain a third container holding a detectably labeled third antibody in lyophilized form or in solution. A kit of this nature can be used in the sandwich assay of the invention. The label or package insert may provide a description of the composition as well as instructions for the intended in vitro or diagnostic use.

The reagents may be provided as dry powders, usually lyophilized, including excipients which on dissolution will provide a reagent solution having the appropriate concentration.

In yet a further aspect of the invention, monoclonal antibodies, or antigen-binding fragment or derivative thereof, as detailed herein are provided labeled with a detectable moiety, such that they may be packaged and used, for example, in kits, to diagnose or identify cells having the aforementioned antigen. Non-limiting examples of such labels include fluorophores such as fluorescein isothiocyanate; chromophores, radionuclides, biotine or enzymes. Such labeled antibodies or binding fragments may be used for the histological localization of the antigen, ELISA, cell sorting, as well as other immunological techniques for detecting or quantifying monomeric/homodimeric CXCR4 r, and cells bearing this antigen, for example.

The invention also includes kits wherein the antibody, or antigen-binding fragment or derivative thereof, is labeled.

Kits are also provided for use as a positive control for purification or immunoprecipitation of monomeric/homodimeric CXCR4 from cells. For isolation and purification of monomeric/homodimeric CXCR4, the kit can contain the antibody described herein, or an antigen-binding fragment or derivative thereof, coupled to beads (e.g., sepharose beads). Kits can be provided which contain the antibodies for detection and quantification of monomeric/homodimeric CXCR4 in vitro or ex vivo, e.g. in an ELISA or a Western blot. The kit comprises a container and a label or package insert on or associated with the container. The container holds a composition comprising at least one antibody, or binding fragment or derivative thereof, of the invention. Additional containers may be included that contain, e.g., diluents and buffers, control antibodies. The label or package insert may provide a description of the composition as well as instructions for the intended in vitro or diagnostic use.

More particularly, the invention concerns a kit for the determination of the monomeric/homodimeric CXCR4 status of a tumor by any method known by the man skilled in the art. In a preferred embodiment, as it will be described in the experimental examples, the invention relates to a kit for the determination of the monomeric/homodimeric CXCR4 status of a tumor by IHC methods or FACS.

In a particular embodiment, the kit of the invention comprises at least an anti-monomeric/homodimeric CXCR4 antibody, or an antigen-binding fragment or derivative thereof, as above described, said antibody being preferably labeled.

In a preferred embodiment, the kit for detecting in vitro the presence and/or the location of a monomeric/homodimeric CXCR4-expressing tumor in a subject, further comprises a reagent for detecting the extent of binding between the said anti-CXCR4 antibody and monomeric/homodimeric CXCR4.

The kit according to the invention may further comprise a reagent for quantifying the level of binding between the said antibody, or antigen-binding fragment or derivative thereof, and monomeric/homodimeric CXCR4.

In still another embodiment, the kit according to the invention further comprises positive and negative control samples for the scoring of monomeric/homodimeric CXCR4 expression level.

The said kit can further comprise a polyclonal antibody recognizing specifically murine antibodies. Advantageously, the said polyclonal antibody is labeled.

Other characteristics and advantages of the invention appear in the continuation of the description with the examples and the figures whose legends are represented below.

EXAMPLE 1

Anti-CXCR4 427aB1 Monoclonal Antibody (Mab) Generation (F50067-006(5C) 427aB1 cl1B, CNCM Number I-4018)

To generate monoclonal antibodies to CXCR4, Balb/c mice were immunized with recombinant NIH3T3-CXCR4 cells and/or peptides corresponding to CXCR4 extracellular N-term and loops. The mice 6-16 weeks of age upon the first immunization, were immunized once with the antigen in complete Freund's adjuvant subcutaneously (s.c.) followed by 2 to 6 immunizations with antigen in incomplete Freund's adjuvant s.c. The immune response was monitored by retroorbital bleeds. The serum was screened by ELISA (as described bellow) and mice with the higher titers of anti-CXCR4 antibodies were used for fusions. Mice were boost intravenously with antigen two days before sacrifice and removal of the spleen.

ELISA

To select the mice producing anti-CXCR4 antibodies, sera from immunized mice was tested by ELISA. Briefly, microtiter plates were coated with purified [1-41] N-terminal peptide conjugated to BSA at 5 µg equivalent peptide/mL, 100 µL/well incubated at 4° C. overnight, then blocked with 250 µL/well of 0.5% gelatine in PBS. Dilutions of plasma from CXCR4-immunized mice were added to each well and incubated 2 hours at 37° C. The plates were washed with PBS and then incubated with a goat anti-mouse IgG antibody conjugated to HRP (Jackson Laboratories) for 1 hour at 37° C. After washing, plates were developed with TMB substrate, the reaction was stopped 5 min later by addition of 100 µL/well 1M $H_2SO_4$. Mice that developed the highest titers of anti-CXCR4 antibodies were used for antibody generation.

Generation of Hybridomas Producing Mabs to CXCR4

The mouse splenocytes, isolated from a Balb/c mice that developed the highest titers of anti-CXCR4 antibodies were fused with PEG to a mouse myeloma cell line Sp2/0. Cells were plated at approximately $1\times10^5$/well in microtiter plates followed by two weeks incubation in selective medium containing ultra culture medium+2 mM L-glutamine+1 mM sodium pyruvate+1×HAT. Wells were then screened by ELISA for anti-CXCR4 monoclonal IgG antibodies. The antibody secreting hybridomas were then subcloned at least twice by limiting dilution, cultured in vitro to generate antibody for further analysis.

EXAMPLE 2

427aB1 Mab Recognizes Both CXCR4 Monomers and Homodimers on Cell Lysates

Figure 1:
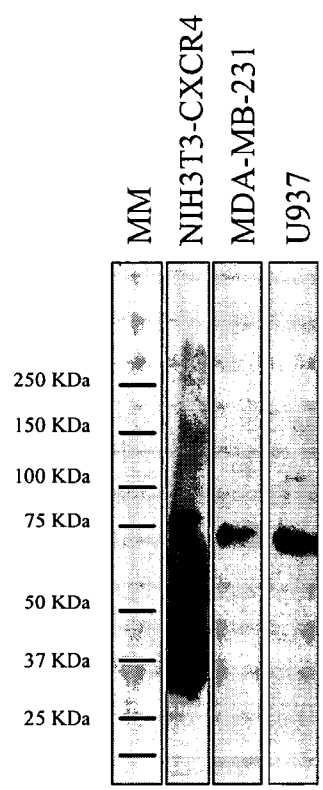
FIG. 1 shows that 427aB1 Mab recognizes both CXCR4 monomers and homodimers on cell lysates.

NIH3T3-hCXCR4 transfected cells, MDA-MB-231 (breast) and U937 (AML) cancer cells were washed twice in PBS. Then $100 \cdot 10^6$ cells/ml were submitted to lysis using the following buffer: 20 mM TrisHCl pH8.5, 100 mM $(NH_4)_2SO_4$, 10% glycerol, 1% CHAPSO and 1% protease inhibitors cocktail for 30 min at 4° C. The cell lysate was collected by centrifugation at 10 000 g at +4° C. for 20 min and analyzed by western blot using 427aB1 Mab as primary antibody. FIG. 1 shows that Mab 427aB1 recognizes both CXCR4 monomers and homodimers in NIH3T3-CXCR4. Cancer cell lines MDA-MB-231 and U937 seem to express CXCR4 mainly as homodimers.

EXAMPLE 3

427aB1 Mab Immunoprecipitates Both CXCR4 Monomers and Homodimers

NIH3T3-CXCR4 cell pellets were washed with 20 mM TrisHCl, pH 8.5 containing 100 mM $(NH4)_2SO_4$ and then suspended in lysis buffer (20 mM TrisHCl, pH 8.5 containing 100 mM $(NH4)_2SO_4$, 10% glycerol, 1% CHAPSO and 10 µL/mL protease inhibitor cocktail). Cells were disrupted with Potter Elvehjem homogenizer. The solubilized membranes were collected by centrifugation at 105000 g at +4° C. for 1 h, then incubated overnight at +4° C. with 427aB1 Mab-coupled Sepharose 4B beads and mixture was poured into a glass column and washed with lysis buffer. The proteins captured by 427aB1 Mab were eluted and analyzed by western blot using 427aB1 Mab as primary antibody. Interesting fractions were pooled, concentrated and used for both WB analysis and preparative SDS-PAGE resolution (4-12% Bis-Tris gel). After silver staining, the bands of interest were excised from the gel and submitted to in-gel digestion using an automated protein digestion system, MassPREP station (Waters, Milford, Mass., USA). The gel spots were washed twice with 50 µL of 25 mM $NH_4HCO_3$ (Sigma, Steinheim, Germany) and 50 µL of acetonitrile (Carlo Erba Reactifs-SDS, Val de Reuil, France). The cysteine residues were reduced at 60° C. for 1 hour by 50 µL of 10 mM DTT prepared in 25 mM $NH_4HCO_3$ and alkylated at room temperature for 20 minutes by 50 µL of 55 mM iodoacetamide (Sigma) prepared in 25 mM $NH_4HCO_3$. After dehydration of the gel spots with acetonitrile, the proteins were digested overnight in gel by adding 10 µL of 12.5 ng/µl modified porcine trypsin (Promega, Madison, Wis., USA) in 25 mM $NH_4HCO_3$ at room temperature. The generated peptides were extracted with 35 µL of 60% acetonitrile containing 5% formic acid (Riedel-de Haën, Seelze, Denmark) followed by removing acetonitrile excess and were subjected to nano-LC-MS/MS. Mass data collected during nanoLC-MS/MS analysis were processed and converted into *.mgf files to be submitted to the MASCOT™ search engine. Searches were performed with a tolerance on measurements of 0.25 Da in MS and MS/MS modes.

Figure 2:
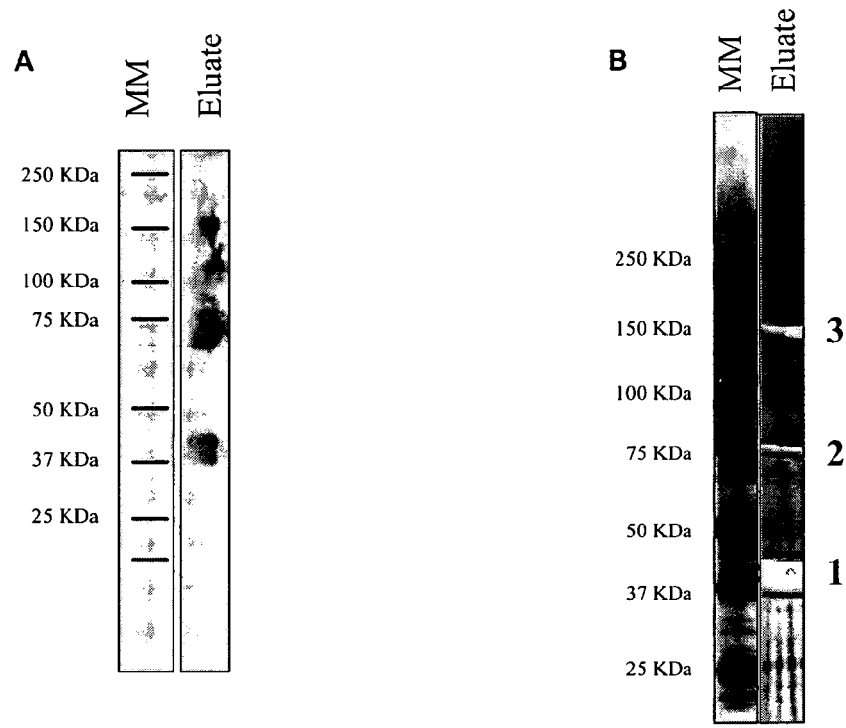
FIGS. 2A and 2B show that 427aB1 Mab immunoprecipitates both CXCR4 monomers and homodimers.
Figure 3A:
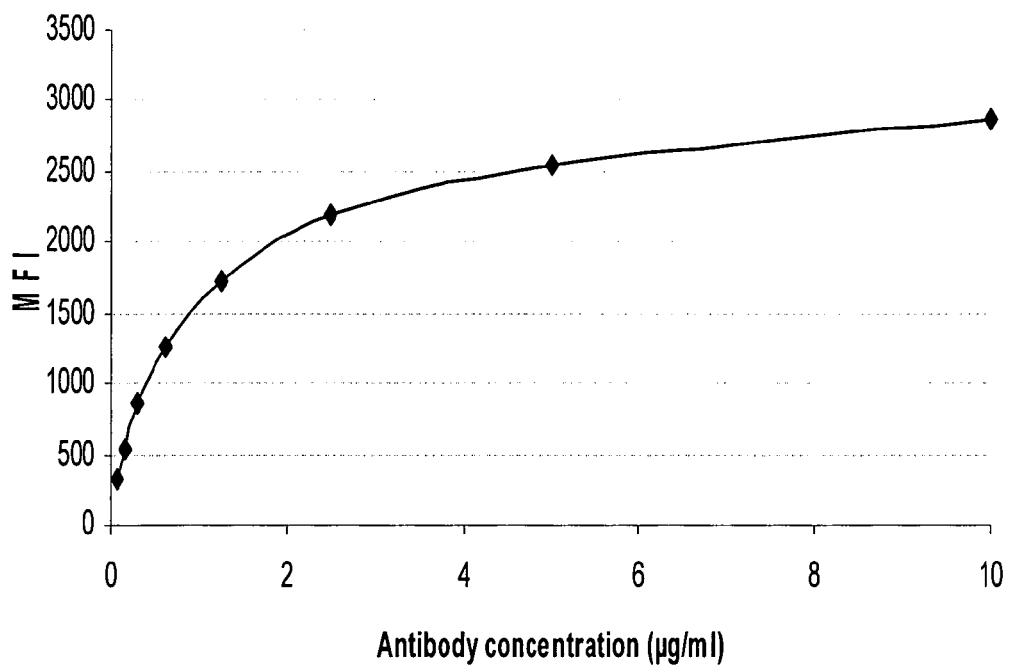
FIGS. 3A, 3B, 3C, 3D and 3E show that 427aB1 Mab recognizes CXCR4 at the cell membrane by FACS analysis.
Figure 3B:
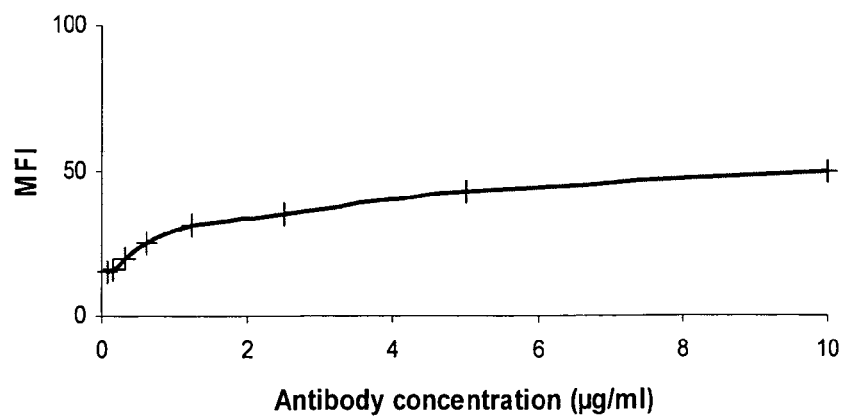
Figure 3C:
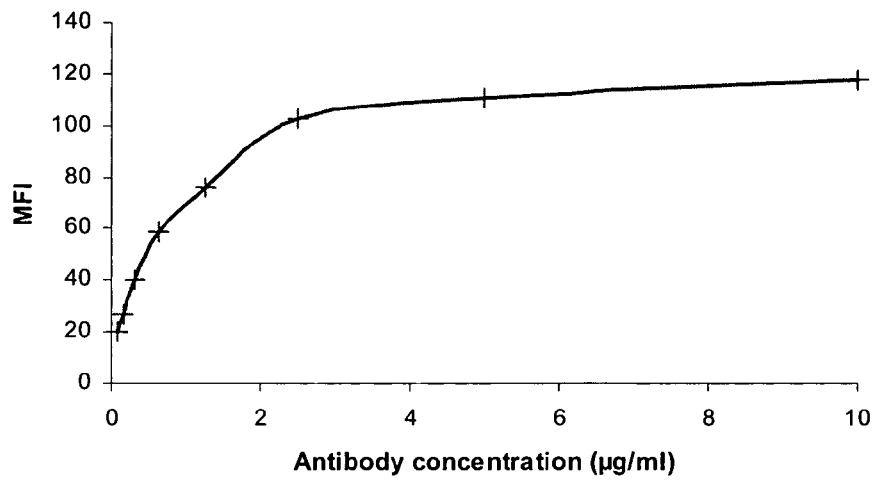
Figure 3D:
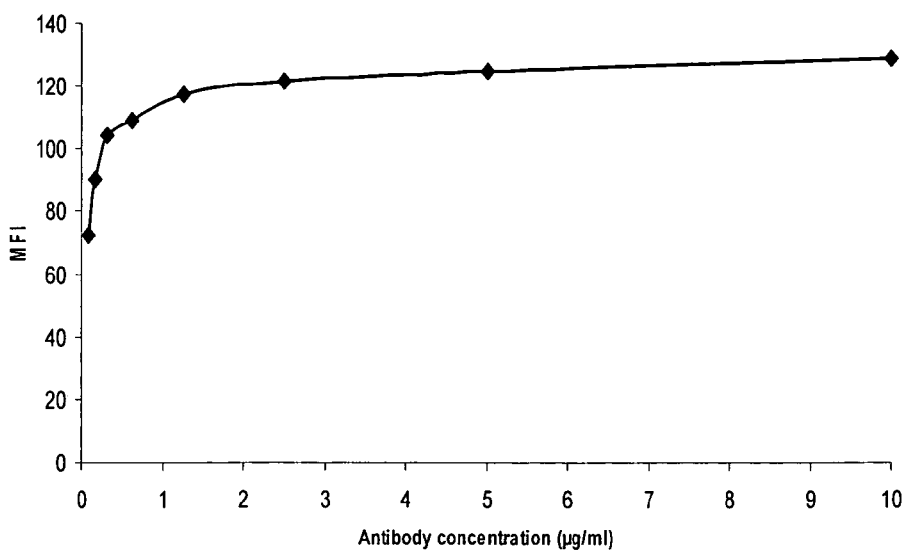
Figure 3E:
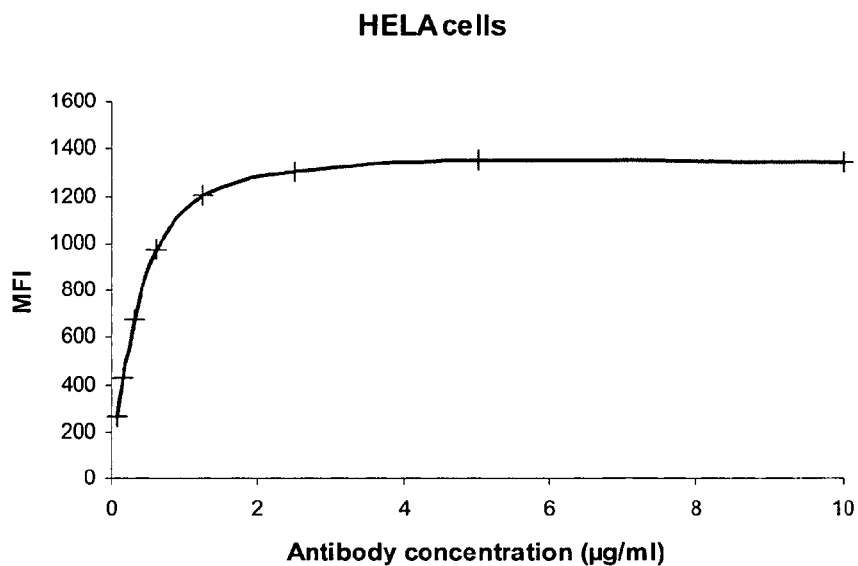

FIG. 2A shows western blot analysis of eluted concentrated fractions after immunoprecipitation using 427aB1

Mab-coupled Sepharose beads. Three bands at 37-43, 75 and 150 kDa apparent molecular weights were recognized by 427aB1 Mab.

Eluted concentrated fraction after immunoprecipitation using 427aB1 Mab-coupled Sepharose beads was also resolved by SDS-PAGE and visualized by silver staining. The bands at 37-43, 75 and 150 KDa were excised from gel (FIG. 2B), digested with trypsin and analyzed by LC-MS/MS as described above. The collected peak lists were submitted to Mascot for peptide sequence database search. CXCR4 was identified in all bands:

Six CXCR4 peptides were identified in the 37-43-kDa band (band number 1) via the MASCOT™ search engine: 31-38 peptide EENANFNK, contained in N-terminal; 135-146 peptide YLAIVHATNSQR and 135-148 peptide YLAIVHATNSQRPR, and 184-188 peptide YICDR, contained in extra-cellular loop 2; 272-282 peptide QGCEFENTVHK, contained in extra-cellular loop 3 and 311-322 peptide TSAQHALTSVSR contained in C-terminal.

The 75-kDa band (band number 2) contained five CXCR4 peptides: 31-38 peptide EENANFNK, contained in N-terminal CXCR4; 135-146 peptide YLAIVHATNSQR, contained in intra-cellular loop 2; 135-148 peptide YLAIVHATNSQRPR, contained in intra-cellular loop 2; 272-282 peptide QGCEFENTVHK, contained in extra-cellular loop 3 and 311-322 peptide TSAQHALTSVSR, contained in C-terminal. Said peptides were identified via the MASCOT™ search engine In the 150-kDa band (band number 3), two CXCR4 peptides were identified via the MASCOT™ search engine. 31-38 peptide EENANFNK, contained in N-terminal and 311-322 peptide TSAQHALTSVSR, contained in C-terminal.

The results obtained in this study clearly show that 427aB1 Mab immunoprecipitates CXCR4. In addition, 427aB1 Mab recognizes CXCR4 both as a monomer and a homodimer.

EXAMPLE 4

427aB1 Mab Recognizes CXCR4 Localized at the Cell Membrane by FACS Analysis

In this experiment, specific binding to human CXCR4 of 427aB1 Mab was assessed by FACS analysis.

NIH3T3, NIH3T3-hCXCR4 transfected cells, MDA-MB-231, Hela, HT-29 and U937 cancer cell lines were incubated with 427aB1 monoclonal antibody (0-10 µg/mL). The cells were then washed with 1% BSA/PBS/0.01% NaN3. Next, Alexa-labeled secondary antibodies were added to the cells and were allowed to incubate at 4° C. for 20 min. The cells were then washed again twice. After the second wash, FACS analysis was performed.

Results of these binding studies are provided in FIG. 3 They show that 427aB1 binds to human CXCR4-NIH3T3 transfected cell line (FIG. 3A), but not to the parent NIH3T3 cells (not shown). This Mab was also capable to recognizing human cancer cell lines, for examples HT-29 colon cancer cells (FIG. 3B), MDA-MB-231 breast cancer cells (FIG. 3C), U937 promyelocytic cancer cells (FIG. 3D) and Hela cervix cancer cells (FIG. 3E), suggesting that these cell lines naturally express CXCR4 monomers and/or homodimers.

EXAMPLE 5

427aB1 Mab Binds to CXCR4 at Cell Membrane Even in the Presence of the Anti-CXCR4 515H7 Therapeutic Mab by FACS Analysis In this experiment, competition of binding to human CXCR4 of anti-CXCR4 Mabs 427aB1 and 515H7 was examined by FACS analysis.

Figure 4A:
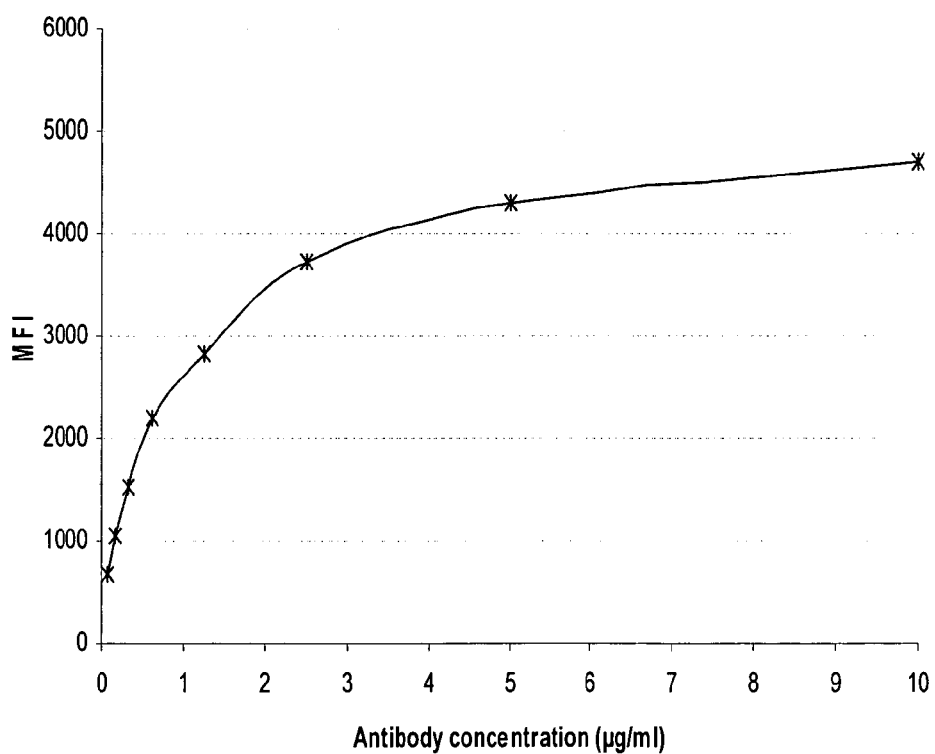
FIGS. 4A and 4B illustrate that 427aB1 Mab binds to CXCR4 at cell membrane even in the presence of the anti-CXCR4 515H7 therapeutic Mab by FACS analysis.
Figure 4B:
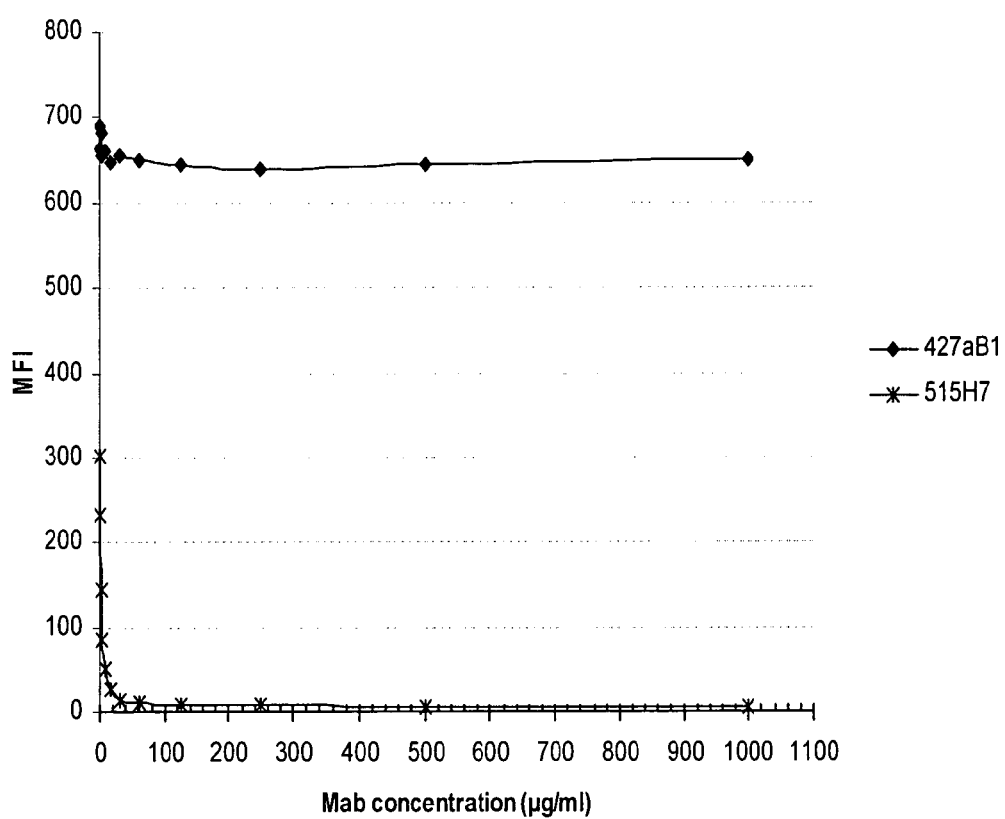

NIH3T3-hCXCR4 transfected cells, were first incubated with biotinylated 515H7 Mab (5 µg/ml) [which recognized NIH3T3-CXCR4 cells (FIG. 4A)], and then either 427aB1 Mab or 515H7 Mab (0-1 mg/mL) for 1 hour at 4° C. The cells were then washed with 1% BSA/PBS/0.01% NaN3. Next, labeled-streptavidin was added to the cells and was allowed to incubate at 4° C. for 20 min, before another couple of washes. After the second wash, FACS analysis was performed. Results of these binding studies are provided in FIG. 4B and showed that anti-CXCR4 Mab 427aB1 binds to human CXCR4-NIH3T3 transfected cells even in the presence of 515H7 Mab. In contrast, the presence of biotinylated 515H7 Mab inhibited the binding of non-labeled 515H7 Mab to CXCR4, as expected.

EXAMPLE 6

427aB1 Mab does not Modulate CXCR4/CXCR2 Heterodimers Conformation by BRET Analysis This functional assay allows the evaluation of the conformational changes induced upon SDF-1 and/or 427aB1 Mab binding to CXCR4 receptor at the level of CXCR2/CXCR4 heterodimer.

Expression vectors for each of the investigated interaction partners were constructed as fusion proteins with the corresponding dye (*Renilla reniformis* luciferase, Rluc and Yellow fluorescent protein, YFP) by applying conventional molecular biology techniques. Two days prior performing BRET experiments, HEK293 cells were transiently transfected with expression vectors coding for the corresponding BRET partners: [CXCR4-Rluc+CXCR2-YFP]. The next day, the cells were distributed in poly-lysine pre-coated white 96 MW plates in complete culture medium [DMEM supplemented with 10% FBS]. Cells were first cultivated at 37° C. with $CO_2$ 5% in order to allow cell attachment to the plate. Cells were then starved with 200 µl DMEM/well overnight. Immediately prior to the BRET experiment, DMEM was removed and cells were quickly washed with PBS. Cells were then incubated in PBS in the presence or absence of antibody, 15 min at 37° C. prior to the addition of coelenterazine H 5 µM with or without SDF-1 in a final volume of 50 µl. After incubation for 5 minutes at 37° C. and further incubation for 20 min at room temperature, light-emission acquisition at 485 nm and 530 nm was initiated using the Mithras LB940 multilabel reader (Berthold) (1 s/wavelength/well repeated 15 times at room temperature).

Calculation of BRET ratio was performed as previously described (Angers et al., 2000): [(emission$_{530\ nm}$)−(emission$_{485\ nm}$)×Cf]/(emission$_{485\ nm}$), where Cf=(emission$_{530\ nm}$)/(emission$_{485\ nm}$) for cells expressing the Rluc fusion protein alone under the same experimental conditions. Simplifying this equation shows that BRET ratio corresponds to the ratio 530/485 nm obtained when the two BRET partners are present, corrected by the ratio 530/485 nm obtained under the same experimental conditions, when only the partner fused to Rluc is present in the assay. For sake of readability, results are expressed as percentage of the basal signal.

Figure 5:
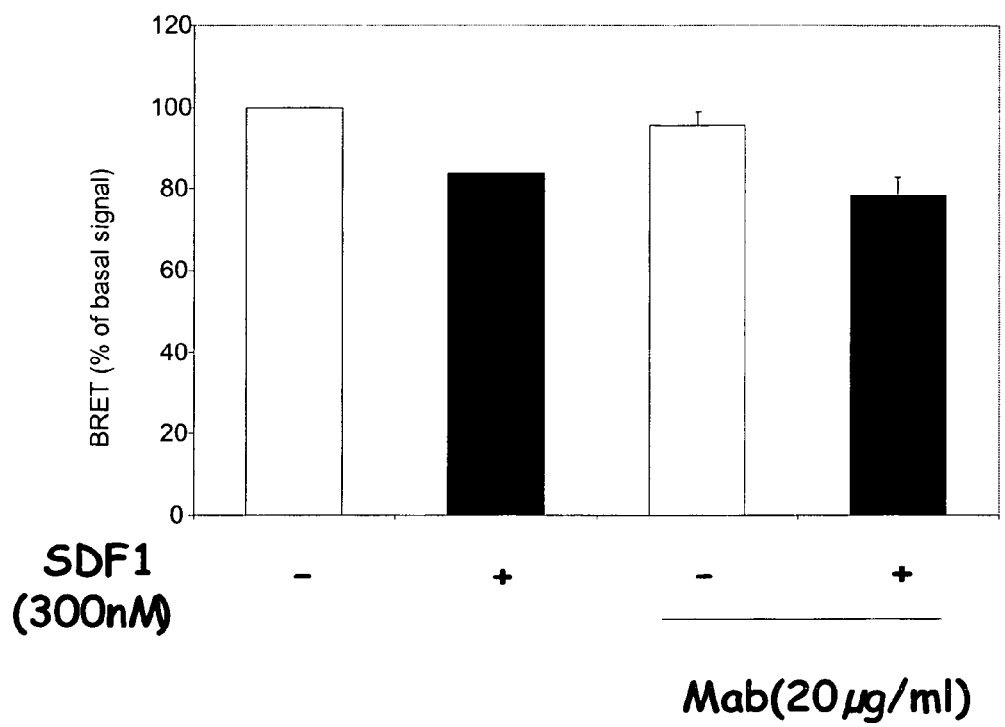
FIG. 5 shows that 427aB1 Mab does not modulate CXCR4/CXCR2 hetero-dimers conformation

SDF1 (300 nM) decreased by about 20% the BRET signal resulting from the spatial proximity of CXCR4 and CXCR2 receptors. It is likely to indicate CXCR4/CXCR2 heterodimers formation or conformational changes of pre-existing dimers (FIG. 5). 427aB1 Mab did not modulate SDF-1-induced conformational changes for CXCR2/CXCR4 heterodimer and did not modulate by itself CXCR4/CXCR2 spatial proximity. This indicates that 427aB1 Mab has no influence on CXCR4/CXCR2 heterodimers conformation (FIG. 5).

EXAMPLE 7

427aB1 Mab Activity Evaluation in MDA-MB-231 Xenograft Tumor Growth Model in Nod/Scid Mice The goal of this experiment was to assess the inhibitory activity of anti-CXCR4 Mab 427aB1 against an MDB-MB-231 xenograft in Nod/Scid mice.

MDA-MB-231 cells from ECACC were routinely cultured in DMEM medium (Invitrogen Corporation, Scotland, UK), 10% FCS (Sigma, St Louis Md., USA). Cells were split 48 hours before engraftment so that they were in exponential phase of growth. Ten million MDA-MB-231 cells were engrafted in PBS to 7 weeks old Nod/Scid mice (Charles River, France). Five days after implantation, tumors were measurable (34 mm$^3$<V$^3$<40 mm$^3$) and animals were divided into groups of 6 mice with comparable tumor size. Mice were treated i.p. with a 2 mg/mouse loading dose of Mab 427aB1. Then, mice were injected twice a week at 1 mg/dose/mouse of Mab 427aB1. A PBS group was introduced as a control group in this experiment. Tumor volume was measured twice a week and calculated by the formula: $\pi/6 \times length \times width \times height$. Statistical analyses were performed at each measure using a Mann-Whitney test.

Figure 6:
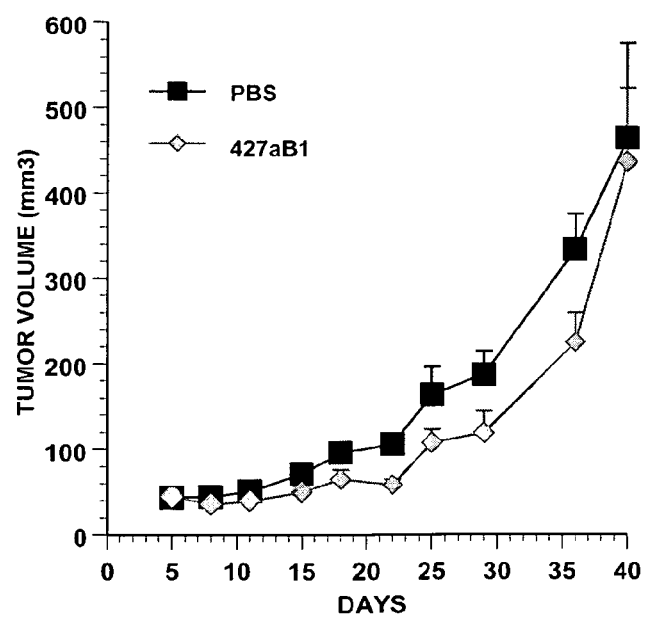
FIG. 6 shows that 427aB1 Mab has no effect on MDA-MB-231 xenograft tumor growth model in Nod/Scid mice.

No mortality was observed during treatment. Compared to the PBS control group, no significant inhibition of tumor growth at D40 (p=0.485) for 427aB1 Mab 1 mg/dose was observed. In addition, the average tumor volume after 5 weeks of treatment was not reduced by Mab 427aB1 versus PBS (FIG. 6).

EXAMPLE 8

427aB1 Mab Recognizes CXCR4 Present at the Cell Membrane (Paraffin Embedded Tumors IHC Staining)

Sections were deparaffinized, rehydrated, and placed at 98° C. for 5 minutes in pre-warm at 98° C. EDTA pH8 for heat-induced epitope retrieval and for 5 additional minutes at room temperature in the warm EDTA buffer. Slides were then rinsed in tap water for 5 minutes. After 3 washes in Tris Buffer Saline-0.05% Tween 20 (TBS-T) (Dako S3006), the endogenous peroxidase activity was blocked using Peroxidase Blocking Reagent (Dako K4007) for five minutes. Sections were washed with TBS-T and incubated in blocking reagent (UltraV block-TA-125UB—LabVision) for 5 minutes before incubation with the anti-CXCR-4 mouse monoclonal antibody (5 µg/ml, clone 427aB1, Pierre Fabre) or mouse IgG1/kappa (5 µg/ml, X0931, Dako) as an isotype control overnight at 4° C. Sections were washed with TBS-T and incubated with SignalStain Boost IHC detection Reagent (HRP, M) for 30 minutes at room temperature. Diaminobenzidine was used for development of a brown reaction product (Dako K3468). The slides were immersed in hematoxylin for 4 minutes to counterstain (Dako S3309) and washed in PBS before being mounted in Faramount mounting medium plus coverslipe. In this immunohistochemistry procedure, the brown reaction product correlates to positive staining of the cell membrane and lack of brown reaction product correlates to negative staining and no visualization of the cell membrane.

Figure 7:
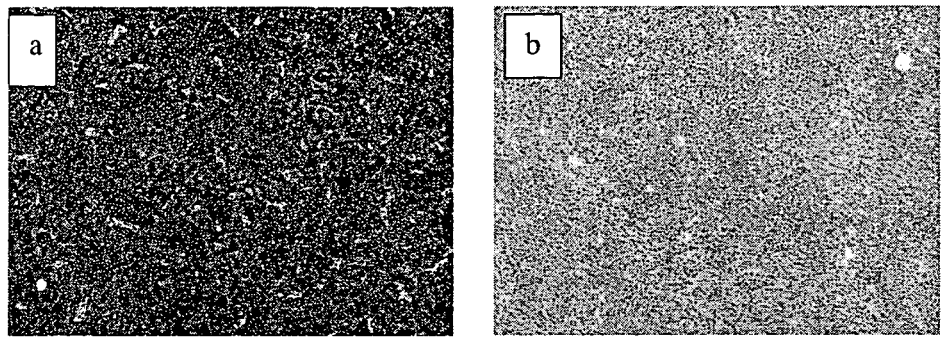
FIG. 7 shows a) IHC staining using m427aB1 and b) IHC staining using mIgG1 on RAMOS.
Figure 8:
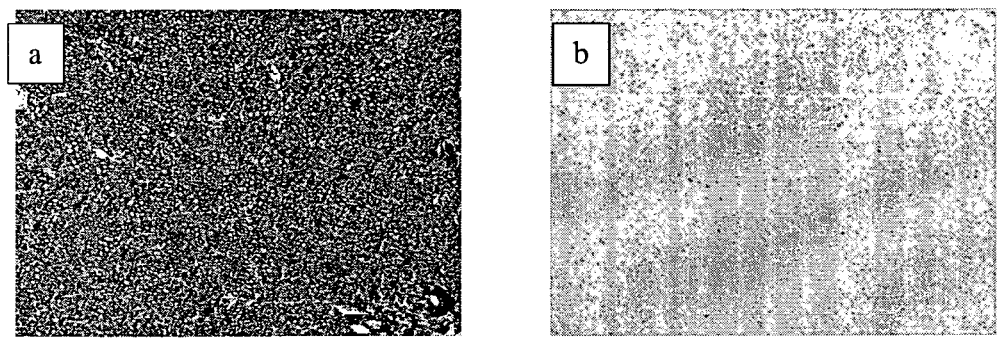
FIG. 8 shows a) IHC staining using 427aB1 and b) IHC staining using mIgG1 on KARPAS299 xenograft tumors.

The 427aB1 Mab differentially stains the cell membrane of various tumor types. FIGS. 7 and 8 illustrated staining performed in 2 xenograft models in which an anti-tumoral activity with the therapeutic anti-CXCR-4 hz515H7 antibody has been described: RAMOS and KARPAS299.

As shown in FIGS. 7 and 8, the expression detected is lower in KARPAS299 (FIG. 8) than in RAMOS (FIG. 7). This data correlates nicely with the study of the CXCR-4 expression by flow cytometry. Indeed, RAMOS cells express about 5 levels more of CXCR-4 than KARPAS299 one (Antibody Binding Capacity: 200 000 for RAMOS and 40 000 for KARPAS299). Membranous staining is weaker in KARPAS299 (FIG. 8), whereas, membranous staining is significantly higher in RAMOS (FIG. 7).

The invention claimed is:

1. An anti-CXCR4 antibody, or a CXCR4-binding fragment thereof, comprising i) a heavy chain comprising the following three CDRs, respectively CDR-H1 having the sequence SEQ ID No. 1, CDR-H2 having the sequence SEQ ID No. 2, and CDR-H3 having the sequence SEQ ID No. 3; and ii) a light chain comprising the following three CDRs, respectively CDR-L1 having the sequence SEQ ID No. 4, CDR-L2 having the sequence SEQ ID No. 5, and CDR-L3 having the sequence SEQ ID No. 6.

2. The antibody of claim 1, or a CXCR4-binding fragment thereof, wherein the said antibody is selected among:
   a. an antibody with a heavy chain comprising the following three CDRs, respectively CDR-H1 having the sequence SEQ ID No. 1, CDR-H2 having the sequence SEQ ID No. 2 and CDR-H3 having the sequence SEQ ID No. 3; and a light-chain variable domain comprising the sequence SEQ ID No. 8;
   b. an antibody with a heavy chain variable domain comprising the sequence SEQ ID No. 7; and a light chain comprising the following three CDRs, respectively CDR-L1 having the sequence SEQ ID No. 4, CDR-L2 having the sequence SEQ ID No. 5 and CDR-L3 having the sequence SEQ ID No. 6; or
   c. an antibody with a heavy chain variable domain comprising the sequence SEQ ID No. 7; and a light-chain variable domain comprising the sequence SEQ ID No. 8.

3. The antibody according to claim 1, or a CXCR4-binding fragment thereof, wherein said antibody is a murine antibody.

4. A murine hybridoma capable of secreting an antibody or a CXCR4-binding fragment thereof, said murine hybridoma being deposited at the CNCM, Institut Pasteur, Paris, France on Jun. 25, 2008 under the number I-4018.

5. A method for detecting the presence of a tumor expressing monomeric/homodimeric CXCR4 in a subject, wherein said process comprises the steps of:
   (a) contacting a tumor sample from the said subject with an antibody, or a CXCR4-binding fragment thereof, according to claim 1 or produced by a hybridoma according to claim 4;
   (b) detecting the binding of the said antibody, or a CXCR4-binding fragment thereof, with the tumor sample, wherein said binding indicates the presence of a tumor expressing monomeric/homodimeric CXCR4 in said subject.

6. A method for determining the percentage of cells expressing CXCR4 as monomer and/or homodimer in a tumor from a subject, said method comprising the steps of:
   (a) contacting a tumor sample from the subject with an antibody, or a CXCR4-binding fragment thereof, according to claim 1 or produced by a hybridoma according to claim 4; and
   (b) quantifying the percentage of cells expressing CXCR4 as monomer and/or homodimer in the sample.

7. A method for determining the expression level of monomeric/homodimeric CXCR4 as monomer and/or homodimer in a tumor from a subject, said method comprising the steps of:
   (a) contacting a tumor sample from the subject with an antibody or a CXCR4-binding fragment thereof, according to claim 1 or produced by a hybridoma according to claim 4; and
   (b) quantifying the level of binding of the said antibody, or a CXCR4-binding fragment thereof, to monomeric/homodimeric CXCR4 in the tumor sample.

8. The method of claim 7, wherein the level of binding of the said antibody, or a CXCR4-binding fragment thereof, to monomeric/homodimeric CXCR4 is measured by immunohistochemistry (IHC) or FACS, preferably by IHC.

9. A method for determining the scoring of a tumor from a subject, said method comprising:
   (a) contacting a tumor sample from the subject with an antibody, or or a CXCR4-binding fragment thereof, according to claim 1 or produced by a hybridoma according to claim 4;
   (b) quantifying the level of binding of said antibody, or or a CXCR4-binding fragment thereof, to monomeric/homodimeric CXCR4 as monomer and/or homodimer in the said tumor sample; and
   (c) scoring the tumor by comparing the quantified level of binding of the said antibody, or a CXCR4-binding fragment thereof, from the subject to an appropriate scale.

10. The method of claim 9, wherein the said appropriate scale is based on two parameters which are the intensity of the staining and the percentage of positive cells.

11. The method of claim 9, wherein the said appropriate scale is a scale of 0 to 8 wherein "no reactivity" is scored 0, and a strong reactivity in a proportion of "67-100% proportion reactive" is scored 8.

12. A method for determining the status of a tumor from a subject, said method comprising the steps of:
   (a) scoring a tumor from a subject according to claim 9 and
   b) determining that the status of the tumor is [monomeric/homodimeric CXCR4(+)] with a score of 3 to 8; or
   (c) determining that the status of the tumor is [monomeric/homodimeric CXCR4(−)] with a score of 0 to 2.

13. The method of claim 9, wherein the said appropriate scale is a scale of 0 to 3+ wherein no membranous reactivity of tumor cells is scored 0, and strong complete reactivity in more than 10% of tumor cells is scored 3+.

14. A method for determining the status of a tumor from a subject, said method comprising the steps of:
   (a) scoring a tumor from a subject according to claim 10; and
   (b) determining that the status of the tumor is [monomeric/homodimeric CXCR4(+)] with a score of 2+ or 3+; or
   (c) determining that the status of the tumor is [monomeric/homodimeric CXCR4(−)] with a score of 0 or 1+.

15. A kit comprising at least an antibody, or a CXCR4-binding fragment thereof, according to claim 1 or produced by a hybridoma according to claim 4.

16. The kit of claim 15, characterized in that said antibody, or a CXCR4-binding fragment thereof, is labeled.

17. The kit of claim 15, further comprising positive and negative control samples for the scoring of monomeric/homodimeric CXCR4 expression level.

* * * * *

UNITED STATES PATENT AND TRADEMARK OFFICE
CERTIFICATE OF CORRECTION

PATENT NO. : 9,518,120 B2
APPLICATION NO. : 14/235274
DATED : December 13, 2016
INVENTOR(S) : Klinguer-Hamour et al.

Page 1 of 1

It is certified that error appears in the above-identified patent and that said Letters Patent is hereby corrected as shown below:

In the Claims

Claim 4, Column 40, Line 56, delete "or a CXCR4-binding fragment thereof".

Claim 9, Column 41, Line 30, delete second instance of "or".

Claim 9, Column 41, Line 33, delete second instance of "or".

Signed and Sealed this
Seventh Day of March, 2017

Michelle K. Lee
*Director of the United States Patent and Trademark Office*